United States Patent [19]
Bondinell et al.

[11] Patent Number: 6,117,866
[45] Date of Patent: Sep. 12, 2000

[54] BICYCLIC FIBRINOGEN ANTAGONISTS

[75] Inventors: William Edward Bondinell, Wayne; James Martin Samanen, Phoenixville, both of Pa.

[73] Assignee: SmithKline Beecham Corporation, Philadelphia, Pa.

[21] Appl. No.: 08/875,359

[22] PCT Filed: Jan. 9, 1995

[86] PCT No.: PCT/US95/00248

§ 371 Date: Jul. 3, 1996

§ 102(e) Date: Jul. 3, 1996

[87] PCT Pub. No.: WO96/18619

PCT Pub. Date: Jul. 13, 1995

Related U.S. Application Data

[63] Continuation-in-part of application No. 08/179,011, Jan. 7, 1994, abandoned.

[51] Int. Cl.$^7$ .................. A61K 31/5513; C07D 243/14; A61P 7/02
[52] U.S. Cl. .................. 514/221; 514/213; 540/504; 540/512; 540/513; 540/514; 540/523
[58] Field of Search .................. 540/504, 512, 540/513, 514, 523; 514/213, 221

[56] References Cited

U.S. PATENT DOCUMENTS

| 4,297,346 | 10/1981 | Rips et al. ............... 424/127 |
| 4,322,436 | 3/1982 | Korosi et al. ............... 260/239 BD |

(List continued on next page.)

FOREIGN PATENT DOCUMENTS

| 045 451 | 2/1982 | European Pat. Off. . |
| 048 045 | 3/1982 | European Pat. Off. . |
| 275 748 | 7/1988 | European Pat. Off. . |
| 341 915 | 11/1989 | European Pat. Off. . |
| 372 486 | 8/1990 | European Pat. Off. . |
| 381 033 | 8/1990 | European Pat. Off. . |
| 447 857 | 9/1991 | European Pat. Off. . |
| 478 328 | 4/1992 | European Pat. Off. . |
| 478 362 | 4/1992 | European Pat. Off. . |
| 478 363 | 4/1992 | European Pat. Off. . |
| 479 481 | 4/1992 | European Pat. Off. . |
| 512 829 | 11/1992 | European Pat. Off. . |
| 523 845 | 1/1993 | European Pat. Off. . |
| 3702755 | 8/1988 | Germany . |
| WO 89/05150 | 6/1989 | WIPO . |
| WO 92/07568 | 5/1992 | WIPO . |
| WO 92/09297 | 6/1992 | WIPO . |
| WO 93/00095 | 1/1993 | WIPO . |
| WO 93/08174 | 4/1993 | WIPO . |
| WO 94/11360 | 5/1994 | WIPO . |
| WO 94/14776 | 7/1994 | WIPO . |
| WO 95/04057 | 2/1995 | WIPO . |
| WO 96/00574 | 1/1996 | WIPO . |

OTHER PUBLICATIONS

Friedinger, R.M., Cholecystokinin and Gastrin Antagonists, *Med. Res. Rev.*, 9, 271 (1989).

Mori et al., New Synthesis of Diazepinone Skeleton Using Palladium Catalyzed Carbonylation, *Heterocycles*, 16 (1981).

Muller et al., Synthese von 1, 2–annelierten 1,4–Benzodiazepinen und 4, 1–Benzoxazepinen, *Helv. Chim. Acta*, 65, 2118 (1982).

Heindel et al., Synthesis, Transformation and General Pharmacologic Activity in 1,4–Benzodiazepine–3,5–Diones, *J. Med. Chem.*, 14, 1233 (1971).

Pauwells et al., Potent and Selective Inhibition of HIV–1 Replication in vitro by a Novel Series of TIBO Derivatives, *Nature*, 343, 470 (1990).

Nichols et al., *J. Pharm. Exp. Ther.*, 270, 614 (1994).

Coller, *Coronary Artery Disease*, 3, 1016 (1992).

Topol et al. *Thrombosis and Haemostasis*, 70, 94 (1993).

Nichols et al., *TIPS*, 13, 413 (Nov. 1991).

Callahan et al., *Peptide Chemistry 1992: Proceedings of the 2nd Japanese Symposium on Peptides Chemistry*, p. 495 (1993).

(List continued on next page.)

*Primary Examiner*—Mukund J. Shah
*Assistant Examiner*—Brenda Coleman
*Attorney, Agent, or Firm*—Charles M. Kinzig

[57] ABSTRACT

Certain compounds within formula (I) are inhibitors of platelet aggregation:

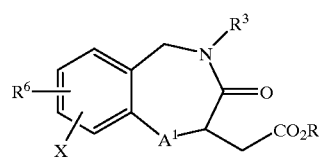

(I)

wherein $A^1$ is NH or $CH_2$;

R is H, $C_{1-6}$alkyl, benzyl or a carboxy protecting group;

$R^3$ is $C_{1-6}$alkyl, Ar-$C_{0-6}$alkyl, $C_{3-7}$cycloalkyl$C_{0-6}$alkyl, or Het-$C_{0-6}$alkyl;

$R^6$ is 4-amidino-Ar-N($CH_3$)CO, [[2-(4-piperidinyl)ethyl](N-methyl)amino]carbonyl, (4,4'-bipiperidin-1-yl)carbonyl, [4-(2-aminoethyl)piperidin-1-yl]carbonyl, [[[3-(4-piperidinyl]propyl]methylamino]carbonyl, 1-[4-(4-pyridyl)piperazinyl]carbonyl, [[2-[(2-amino)pyrid-4-yl]ethyl]methylamino]carbonyl, [[2-(4-piperidinyl)ethyl]carbonyl]amino, [[2-(4-piperidinyl)ethyl]carbonyl]amino, [[2-(1-piperazinyl)ethyl]methylamino]-carbonyl, or [[(1,2,3,4-tetrahydro-7-isoquinolinyl]amino]carbonyl; and X is H, $C_{1-4}$alkyl, $C_{1-4}$alkoxy, $C_{1-4}$alkthio, trifluoroalkyl, N(R')$_2$, $CO_2$R', CON(R')$_2$, OH, F, Cl, Br or I.

16 Claims, No Drawings

U.S. PATENT DOCUMENTS

| | | | |
|---|---|---|---|
| 4,327,026 | 4/1982 | Branca et al. | 260/239.3 D |
| 4,361,511 | 11/1982 | Branca et al. | 260/239.3 D |
| 4,377,522 | 3/1983 | Branca et al. | 260/239.3 |
| 4,410,520 | 10/1983 | Watthey et al. | 424/244 |
| 4,604,389 | 8/1986 | Reiffen et al. | 514/213 |
| 4,737,495 | 4/1988 | Bomhard et al. | 514/213 |
| 4,808,713 | 2/1989 | Attwood et al. | 540/487 |
| 4,820,834 | 4/1989 | Evans et al. | 540/504 |
| 5,008,263 | 4/1991 | Cooper et al. | 514/220 |
| 5,017,571 | 5/1991 | Hansen et al. | 514/213 |
| 5,059,688 | 10/1991 | Effland et al. | 540/594 |
| 5,096,900 | 3/1992 | George et al. | 514/213 |
| 5,149,699 | 9/1992 | Ellingboe et al. | 514/258 |
| 5,241,065 | 8/1993 | Berger et al. | 540/523 |
| 5,250,679 | 10/1993 | Blackburn et al. | 540/490 |
| 5,403,836 | 4/1995 | Blackburn et al. | 514/213 |
| 5,438,118 | 8/1995 | Callahan et al. | 530/330 |
| 5,470,849 | 11/1995 | Callahan et al. | 514/212 |
| 5,565,449 | 10/1996 | Blackburn et al. | 514/219 |
| 5,663,166 | 9/1997 | Blackburn et al. | 514/213 |
| 5,674,863 | 10/1997 | Blackburn et al. | 514/211 |
| 5,674,865 | 10/1997 | Blackburn et al. | 514/213 |
| 5,693,636 | 12/1997 | Bondinell et al. | 514/221 |

OTHER PUBLICATIONS

Ku et al., *J. Am. Chem. Soc.*, 115, 8861–8862 (1993).

Sternbach, L.H., *J. Med Chem.*, 22, 2 (1979).

Tighneanu et al., Double Cyclisation of Phenyglycine–o–carboxylic Acids–I, *Tetrahedron*, 36, 1385 (1980).

Tidwell et al., *Thrombosis Research*, vol. 19, pp. 339–349 (1980).

Ku et al., *J. Med. Chem.*, 38(1), pp. 9–12 (1995).

BICYCLIC FIBRINOGEN ANTAGONISTS

This application is a 371 of PCT/US95/00248 filed Jan. 9, 1995 which is a continuation-in-part of Ser. No. 08/179,011 filed Jan. 7, 1994, now abandoned.

FIELD OF THE INVENTION

This invention relates to novel bicyclic compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess an Arg-Gly-Asp (RGD in single letter amino acid code) sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372,486, EP-A 0 381 033 and EP-A 0 478 363. WO 92/07568 (PCT/US91/08166) discloses fibrinogen receptor antagonists which mimic a conformational γ-turn in the RGD sequence by forming a monocyclic seven-membered ring structure. There remains a need, however, for novel fibrinogen receptor antagonists (e.g. inhibitors of the GPIIb-IIIa protein) which have potent in vivo and in vitro effects and lack the peptide backbone structure of amino acid sequences.

The present invention discloses novel bicyclic compounds including benzazepines and benzodiazepines, which are inhibitors of the GPIIb-IIIa receptor and inhibit platelet aggregation. Certain 5-phenyl-1,4-benzodiazepines are known as a class of drugs which affect the central nervous system, and have been used as anxiolytics. See Sternbach, L. H., *J. Med. Chem.*, 22, 2 (1979). It has also been disclosed that certain 5-phenyl-1,4-benzodiazepines antagonize the effects of cholecystokinin. See Friedinger, *Med. Res. Rev.*, 9, 271 (1989). Certain bicyclic compounds which have fibrinogen antagonist activity are disclosed in WO 93/08174 (PCT/US92/08788), WO 93/00095 (PCT/US/92/05463) and WO 94/14776 (PCT/US93/12436).

SUMMARY OF THE INVENTION

In one aspect this invention is a compound as hereinafter disclosed for inhibiting platelet aggregation.

This invention is also a pharmaceutical composition for inhibiting platelet aggregation or clot formation, which comprises a compound of the invention and a pharmaceutically acceptable carrier.

This invention further comprises the use of a compound as hereinafter described in the manufacture of a medicament for inhibiting platelet aggregation In another aspect, this invention provides a method for inhibiting reocclusion of an artery or vein in a mammal following fibrinolytic therapy or angioplasty, which comprises internally administering an effective amount of a compound of the invention. This invention is also a method for treating stroke, transient ischemia attacks, or myocardial infarction.

DETAILED DESCRIPTION OF THE INVENTION

Although not intending to be bound to any specific mechanism of action, the compounds of this invention are believed to inhibit the binding of fibrinogen to the platelet-bound fibrinogen receptor GPIIb-IIIa, and may interact with other adhesion proteins via antagonism of a putative RGD binding site.

Compounds of this invention are encompassed by formula (I):

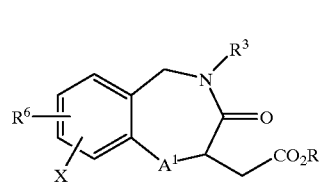

wherein $A^1$ is NH or $CH_2$.

R is H, $C_{1-6}$alkyl, benzyl or a carboxy protecting group. Preferably R is H.

$R^3$ is H, $C_{1-6}$alkyl, $C_{3-6}$alkenyl, Ar-$C_{0-6}$alkyl $C_{3-7}$cycloalkyl$C_{0-6}$alkyl, or Het-$C_{0-6}$alkyl. In particular, $R^3$ may be hydrogen, methyl, isopropyl, n-butyl, isopentyl, 2,2-dimethylbutyl, benzyl, phenylethyl, phenylpentyl, 2-thienylethyl, or cyclohexylethyl, $R^6$ is 4-amidino-Ar-N($CH_3$)CO, 4-amidino-Ar-CONH, [[2-(4-piperidinyl)ethyl]methylamino]carbonyl, (4,4'-bipiperidin-1-yl)carbonyl, [4-(2-aminoethyl)piperidin-1-yl]carbonyl, [[[3-(4-piperidinyl]propyl]methylamino]carbonyl, 1-[4-(4-pyridyl)piperazinyl]carbonyl, [[2-[(2-amino)pyrid-4-yl]ethyl]methylamino]carbonyl, [[2-(4-piperidinyl)ethyl]carbonyl]amino, [[2-(4-piperidinyl)ethyl]carbonyl]amino, [[2-(1-piperazinyl)ethyl]methylamino]carbonyl, [[4-(aminoiminomethyl)phenyl]carbonyl]amino, or [[(1,2,3,4-tetrahydro-7-isoquinolinyl]amino]carbonyl.

X is H, $C_{1-4}$alkyl, $C_{1-4}$alkoxy, $C_{1-4}$alkthio, trifluoroalkyl, $N(R')_2$, $CO_2R'$, $CON(R')_2$, OH, F, Cl, Br or I. Preferably X is H.

Also included in this invention are pharmaceutically acceptable addition salts, complexes or prodrugs of the compounds of this invention. Prodrugs are considered to be any covalently bonded carriers which release the active parent drug according to formula (I) in vivo.

In one subgenus, $A^1$ is NH and forms a 1,4 benzodiazepine which is preferably substituted in the 8 position, and R⁶ is [[2-[(2-amino)pyrid-4-yl]ethyl]methylamino] carbonyl, [[2-(4-piperidinyl)ethyl]methylamino]carbonyl, or [[4-(aminoiminomethyl)-3-fluorophenyl]methylamino] carbonyl. Preferably, R⁶ is [[2-(4-piperidinyl)ethyl] methylamino]carbonyl.

In another subgenus, A¹ is NH and forms a 1,4 benzodiazepine which is substituted in the 7 position, and R⁶ is (4,4'-bipiperidin-1-yl)carbonyl, [[4-(aminoiminomethyl) phenyl]methylamino]carbonyl, [4-(2-aminoethyl)piperidin-1-yl]carbonyl, [[[3-(4-piperidinyl]propyl]methylamino] carbonyl, 1-[4-(4-pyridyl)piperazinyl]carbonyl, or [[(1,2,3, 4-tetrahydro-7-isoquinolinyl]amino]carbonyl. Preferably, R⁶ is (4,4'-bipiperidin-1-yl)carbonyl.

In yet another subgenus, A¹ is CH₂ and forms a 2-benzazepine, which is substituted in the 7 or 8 position, and R⁶ is (4,4'-bipiperidin-1-yl)carbonyl, [[4-(aminoiminomethyl)phenyl]methylamino]carbonyl, [[2-(4-piperidinyl)ethyl]carbonyl]amino, [[2-(4-piperidinyl)ethyl] carbonyl]methylamino, [[4-(aminoiminomethyl)phenyl] carbonyl]amino or [[2-(4-piperidinyl)ethyl]methylamino] carbonyl.

Preferred compounds of this invention are:

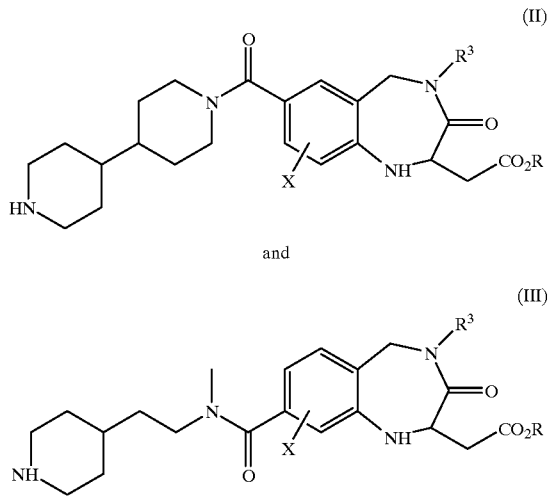

wherein if X is H, R³ is not phenylethyl or, with respect to (III) only, cyclohexylethyl. Such compounds wherein X is H and R³ is phenylethyl or cyclohexylethyl are described in WO 94/14776 and are not a part of this invention.

General compounds of this invention include:
(R,S)-2,3,4,5-tetrahydro-4-methyl-3-oxo-8-[[[2-(4-piperidinyl)ethyl]methylamino]carbonyl]-1H-1,4-benzodiazepine-2-acetic acid;
(R,S)-2,3,4,5-tetrahydro-4-isopentyl-3-oxo-8-[[[2-(4-piperidinyl)ethyl]methylamino]carbonyl]-1H-1,4-benzodiazepine-2-acetic acid;
(R,S)-8-[[[4-(aminoiminomethyl)-3-fluorophenyl] methylamino]carbonyl]-2,3,4,5-tetrahydro-3-oxo-4-(2-phenylethyl)-1H-1,4-benzodiazepine-2-acetic acid;
(R,S)-8-[[(1,2,3,4-tetrahydro-7-isoquinolinyl]amino] carbonyl]-2,3,4,5-tetrahydro-3-oxo-4-(2-phenylethyl)-1H-1,4-benzodiazepine-2-acetic acid;
(R,S)-7-[(4,4'-bipiperidin-1-yl)carbonyl]-4-[2-(cyclohexyl) ethyl]-2,3,4,5-tetrahydro-3-oxo-1H-1,4-benzodiazepine-2-acetic acid;
(R,S)-7-[[4-(2-aminoethyl)piperidin-1-yl]carbonyl]-2,3,4,5-tetrahydro-3-oxo-4-(2-phenylethyl)-1H-1,4-benzodiazepine-2-acetic acid;
(R,S)-7-[[(1,2,3,4-tetrahydro-7-isoquinolinyl]amino] carbonyl]-2,3,4,5-tetrahydro-3-oxo-4-(2-phenylethyl)-1H-1,4-benzodiazepine-2-acetic acid;

(R,S)-7-[(4,4'-bipiperidin-1-yl)carbonyl]-2,3,4,5-tetrahydro-4-methyl-3-oxo-1H-1,4-benzodiazepine-2-acetic acid;
(R,S)-2,3,4,5-tetrahydro-3-oxo-2-(2-phenylethyl)-7-[[[2-(1-piperazinyl)ethyl]methylamino]-carbonyl]-1H-2-benzazepine-4-acetic acid;
(R,S)-2-butyl-2,3,4,5-tetrahydro-3-oxo-7-[[[2-(piperidin-4-yl)-ethyl]methylamino]carbonyl]-1H-2-benzazepine-4-acetic acid;
2-benzyl-2,3,4,5-tetrahydro-3-oxo-7-[[[2-(piperidin-4-yl)-ethyl]methylamino]carbonyl]-1H-2-benzazepine-4-acetate;
2,3,4,5-tetrahydro-3-oxo-2-(5-phenylpentyl)-7-[[[2-(piperidin-4-yl)ethyl]methylamino]carbonyl]-1H-2-benzazepine-4-acetate;
(R,S)-7-[[[4-(aminoiminomethyl)phenyl]methylamino] carbonyl]-2,3,4,5-tetrahydro-2-isopropyl-3-oxo-1H-2-benzazepine-4-acetic acid;
R,S)-2,3,4,5-tetrahydro-2-isopropyl-3-oxo-7-[[[2-(4-piperidinyl)ethyl]methylamino]carbonyl]-1H-2-benzazepine-4-acetic acid;
(R,S)-2,3,4,5-tetraydro-2-isopentyl-3-oxo-7-[[[2-(4-piperidinyl)ethyl]methylamino]carbonyl]-1H-2-benzazepine-4-acetic acid;
(R,S)-2-(3,3-dimethylbutyl)-2,3,4,5-tethydro-3-oxo-7-[[[2-(4-piperdinyl)ethyl]methylamino]carbonyl]-1H-2-benzazepine-4-acetic acid;
(R,S)-2-cyclohexyl-2,3,4,5-tetrahydro-3-oxo-7-[[[2-(4-piperidinyl)ethyl]methylamino]carbonyl]-1H-2-benzazepine-4-acetic acid;
(R,S)-2-[2-(4-fluorophenyl)ethyl]-2,3,4,5-tetrhydro-3-oxo-7-[[[2-(4-piperidinyl)ethyl]methylamino]carbonyl]-1H-2-benzazepine-4-acetic acid;
(R,S)-7-[[[4-(aminoiminomethyl)phenyl]carbonyl]amino]-2,3,4,5-tetrahydro-3-oxo-2-(2-phenylethyl)-1H-2-benzazepine-4-acetic acid;
(R,S)-2-[2-(cyclohexyl)ethyl]-2,3,4,5-tetraydro-3-oxo-7-[[[2-(4-piperidinyl)ethyl]carbonyl]amino]-1H-2-benzazepine-4-acetic acid;
(R,S)-8-[-[(4,4'-bipiperidin-1-yl)carbonyl]-2,3,4,5-terahydro-3-oxo-2-(2-phenylethyl)-1H-2-benzazepine-4-acetic acid;
(R,S)-2,3,4,5-tetrahydro-3-oxo-2-(2-phenylethyl)-7-[[[2-(4-piperidinyl)ethyl]methylamino]carbonyl]-1H-2-benzazepine-4-propionic acid;
(+)-7-[(4,4'-bipiperidin-1-yl)carbonyl]-2,3,4,5-tetrahydro-3-oxo-4-(phenylethyl)-1H-1,4-benzodiazepine-2-acetic acid;
(-)-7-[(4,4'-bipiperidin-1-yl)carbonyl]-2,3,4,5-tetrahydro-3-oxo-4-(phenylethyl)-1H-1,4-benzodiazepine-2-acetic acid;
(R,S)-7-[[(4,4'-bipiperidin-1-yl)]carbonyl]-2,3,4,5-tetrahydro-4-isopropyl-3-oxo-1H-1,4-benzodiazepine-2-acetic acid;
(R)-7-[(4,4'-bipiperidin-1-yl)carbonyl]-2,3,4,5-tetrahydro-4-methyl-3-oxo-1H-1,4-benzodiazepine-2-acetic acid;
(S)-7-[(4,4'-bipiperidin-1-yl)carbonyl]-2,3,4,5-tetrahydro-4-methyl-3-oxo-1H-1,4-benzodiazepine-2-acetic acid;
Sodium (R,S)-7-[(4,4'-bipiperidin-1-yl)carbonyl]-2,3,4,5-tetrahydro-4-methyl-3-oxo-1H-1,4-benzodiazepine-2-acetate;
(R)-2,3,4,5-tetrahydro-4-methyl-3-oxo-8-[[[2-(4-piperidinyl)ethyl]methylamino]carbonyl]-1H-1,4-benzodiazepine-2-acetic acid;
(S)-2,3,4,5-tetrahydro-4-methyl-3-oxo-8-[[[2-(4-piperidinyl)ethyl]methylamino]carbonyl]-1H-1,4-benzodiazepine-2-acetic acid;

(R,S)-8-[[(4,4'-bipiperidin-1-yl)]carbonyl]-2,3,4,5-tetrahydro-2-methyl-3-oxo-1H-2-benzazepine-4-acetic acid;

(R,S)-2,3,4,5-tetrahydro-7-[1-[4-(4-pyridyl)piperazinyl] carbonyl]-4methyl-3-oxo-1H-1,4-benzodiazepine-2-acetic acid;

(R,S)-7-[[[4-(aminoiminomethyl)phenyl]methylamino] carbonyl]-2,3,4,5-tetraydro-2-[2-(2-thienyl)ethyl]-3-oxo-1H-2-benzazepine-4-acetic acid;

(R,S)-2,3,4,5-tetraydro-3-oxo-4-(2-phenylethyll)-7-[[[3-(4-piperidinyl]propyl]methylamino]carbonyl]-1H-1,4-benzodiazepine-2-acetic acid;

(R,S)-2,3,4,5-tetrahydro-4-methyl-3-oxo-7-[[[3-(4-piperidnyl]propyl]methylamino]carbonyl]-1H-1,4-benzodiazepine-2-acetic acid;

(R,S)-2,3,4,5-tetydro-4-isopropyl-3-oxo-8-[[[2-(4-piperidinyl)ethyl]methylamino]carbonyl]-1H-1,4-benzodiazepine-2-acetic acid;

(S)-2,3,4,5-tetrahydro-4-(2-phenylethyl)-3-oxo-8-[[[2-(4-piperidinyl)ethyl]methylamino]carbonyl]-1H-1,4-benzodiazepine-2-acetic acid; and (R,S)-7-[[[4-(aminoiminomethyl)phenyl]carbonyl] methylamino]-2,3,4,5-tetrahydro-3-oxo-2-(2-phenylethyl]-1H-2-benzazepine-4-acetic acid Specific preferred compounds of this invention are (R,S)-2,3,4,5-tetrahydro-4-methyl-3-oxo-8-[[[2-(4-piperidinyl)ethyl]methylamino]carbonyl]-1H-1,4-benzodiazepine-2-acetic acid;

(S)-2,3,4,5-tetrahydro-4-methyl-3-oxo-8-[[[2-(4-piperidinyl)ethyl]methylamino]carbonyl]-1H-1,4-benzodiazepine-2-acetic acid;

(R,S)-2,3,4,5-tetrahydro-3-oxo-4-methyl-8-[[[2-[(2-amino) pyrid-4-yl]ethyl]methylamino]carbonyl]-1H-1,4-benzodiazepine-2-acetic acid;

(R,S)-7-[(4,4'-bipiperidin-1-yl)carbonyl]-2,3,4,5-tetrahydro-4-methyl-3-oxo-1H-1,4-benzodiazepine-2-acetate;

Sodium (R,S)-7-[(4,4'-bipiperidin-1-yl)carbonyl]-2,3,4,5-tetrahydro-4-methyl-3-oxo-1H-1,4-benzodiazepine-2-acetate;

(S)-7-[(4,4'-bipiperidin-1-yl)carbonyl]-2,3,4,5-tetrahydro-4-methyl-3-oxo-1H-1,4-benzodiazepine-2-acetic acid;

Compounds of this invention wherein $R^3$ is H or $C_{1-4}$alkyl, particularly H, methyl or isopropyl, have particularly favorable pharmacological and pharmacokinetic properties.

The meaning of any substituent at any one occurrence is independent of its meaning, or any other substituent's meaning, at any other occurrence, unless specified otherwise. In cases wherein the compounds of this invention may have one or more chiral centers, unless specified, this invention includes each unique nonracemic compound which may be synthesized and resolved by conventional techniques. In general, compounds which have the S configuration at the chiral ring carbon to which the acetate group is attached are preferred.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

$C_{1-4}$alkyl as applied herein is meant to include optionally substituted methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g., that a covalent bond is present).

$C_{3-6}$ alkenyl as applied herein means an optionally substituted alkyl group of 3 to 6 carbons wherein a carbon-carbon single bond is replaced by a carbon-carbon double bond. $C_{3-6}$alkenyl includes 1-propene, 2-propene, 1-butene, 2-butene, isobutene and the several isomeric pentenes and hexenes. Both cis and trans isomers are included.

Ar, or aryl, as applied herein, means phenyl or naphthyl, or phenyl or naphthyl substituted by one to three moieties X. In particular, X may be H, $C_{1-4}$alkyl, $C_{1-4}$alkoxy, $C_{1-4}$alkylthio, trifluoroalkyl, N(R')$_2$, CO$_2$R', CON(R')$_2$, OH, F, Cl, Br or I.

A substituent on a $C_{1-6}$alkyl or $C_{3-6}$alkenyl, such as X, may be on any carbon atom which results in a stable structure, and is available by conventional synthetic techniques.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuran, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro-quinoline and isoquinoline. Any accessible combination of up to three substituents, such as chosen from X, on the Het ring that is available by chemical synthesis and is stable is within the scope of this invention.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from X, on the cycloalkyl ring that is available by conventional chemical synthesis and is stable, is within the scope of this invention.

t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and chex refers to cyclohexyl.

DCC refers to dicyclohexylcarbodiimide, DMAP refers to 4-(dimethylamino) pyridine, DIEA refers to diisopropylethyl amine, EDC refers to N-ethyl-N'-(dimethylaminopropyl)-carbodiimide. HOBt refers to 1-hydroxybenzotriazole, THF refers to tetrahydrofuran, DMF refers to dimethyl formamide, NBS refers to N-bromosuccinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino) phosphonium hexafluorophosphate, HF refers to hydrofluoric acid, TEA refers to triethylamine, TFA refers to trifluoroacetic acid, PCC refers to pyridinium chlorochromate.

Compounds of this invention are prepared by treating, in any order, a compound of the structure:

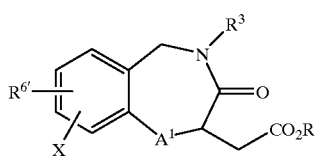

(IV)

wherein $A^1$, X, R and $R_3$ are as defined above, and $R^{6'}$ is $R^6$ wherein any basic nitrogen is protected, with a reagent:
(i) to remove an amino protecting group from $R^{6'}$; and, if necessary,
(ii) to remove a carboxy protecting group from $CO_2R$; and
(iii) form a pharmaceutically acceptable salt thereof.

Illustrative of $R^{6'}$ is $R^6$ wherein the amidino, amino or piperidinyl group is protected by a benyloxy, t-butoxycarbonyl or trifluoroacetyl group.

The compounds of formula (IV) are generally prepared by reacting a compound of the formula (XI) with a compound of the formula (XII):

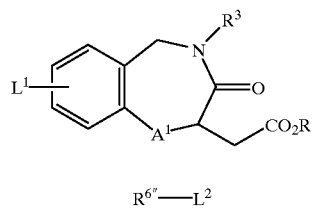

(XI)

(XII)

wherein $A^1$ and $R^3$ are as defined for formula (I), with any reactive functional groups protected, R is $C_{1-6}$alkyl, benzyl or a carboxy protecting group, $L^1$ is $CO_2H$ or NHR', wherein R' is H or $C_{1-4}$alkyl, particularly methyl.

$L^1$ and $L^2$ are functional groups which are capable of reacting to form an amide bond. If $L^1$ is $CO_2H$, then $L^2$ is a basic nitrogen group, such as an amino, methylamino or the nitrogen of a piperidinyl group. For instance $R^{6''}-L^2$ is 4-amidino-Ar-NHR', 2-(4-piperidinyl)(N-methyl)ethylamine, 4-(4-piperidinyl)piperidine, 4-(2-aminoethyl)piperidine, 3-(4-piperidinyl)propyl(N-methyl)amine, 4-(4-pyridyl)piperazine, 2-(2-aminopyrid-4-yl)ethyl(N-methyl)amine or (1,2,3,4-tetrahydro-7-isoquinolinyl)amine, wherein the non-reactive basic nitrogen of the amidino, piperidinyl or amino group is protected by an amino protecting group.

If $L^1$ is NHR', then $L^2$ is a carboxylic acid group, for instance $R^{6''}-L^2$ is 3-(4-piperidinyl)propanoic acid or 4-amidino-Ar-$CO_2H$, wherein the basic nitrogen of the piperidinyl or amidino group is protected.

The compounds of formula (XI) are benzodiazepines and benzazepines, and are prepared by general methods known in the art such as those disclosed in WO 93/00095 (PCT/US/92/05463) and WO 94/14776 (PCT/US93/12436) which are incorporated herein by reference. Compounds of formula (XII) generally contain two basic centers of which one is protected, and are likewise known to the art. See, for instance, WO94/14776.

Coupling reagents as used herein denote reagents which may be used to form amide bonds. Typical coupling methods employ carbodiimides, activated anhydrides and esters, and acyl halides. Reagents such as EDC, DCC, DPPA, PPA, BOP reagent, HOBt, N-hydroxysuccinimide and oxalyl chloride are typical.

Coupling methods to form amide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Solution synthesis for the formation of amide bonds is accomplished using conventional methods used to form amide bonds. Typically, the amine or aniline is coupled via its free amino group to an appropriate carboxylic acids substrate using a suitable carbodiimide coupling agent, such as N,N'-dicyclohexyl carbodiimide (DCC) or EDC, optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a tralkylamine, with isobutyl chloroformate to form the "activated anhydride", which is subsequently reacted with the free amine of a second protected amino acid or aniline.

The reactive functional groups of the sidechains of each synthetic fragment are suitably protected as known in the art. Suitable protective groups are disclosed in Greene, PROTECTIVE GROUPS IN ORGANIC CHEMISTRY, John Wiley and Sons, New York, 1981. For example, the Boc, Cbz, phthaloyl or Fmoc group may be used for protection of an amino (or the nitrogen of a piperidinyl) or amidino group. The Boc group is generally preferred for protection of an amino group. A methyl, ethyl, t-Bu, cHex, benzyl, substituted benzyl, (pivaloyl)methyl or (2-methyl-2-methoxypropanoyl)methyl ester may be used for the protection of the carboxyl group. A benzyl group or suitably substituted benzyl group (e.g., 4-methoxy-benzyl or 2,4-dimethoxy-benzyl) is used to protect the mercapto group or the hydroxyl group. The tosyl group may be used for protection of the imidazolyl group and tosyl or nitro group for protection of the guanidino group. A suitably substituted carbobenzyloxy group or benzyl group may be also be used for the hydroxyl group or amino group. Suitable substitution of the carbobenzyloxy or benzyl protecting groups is ortho and/or para substitution with chloro, bromo, nitro, methoxy or methyl, and is used to modify the reactivity of the protective group. Except for the Boc group, the protective groups for the amino moiety are, most conveniently, those which are not removed by mild acid treatment. These protective groups are removed by such methods as catalytic hydrogenation, sodium in liquid ammonia or HF treatment, as known in the art.

Methods for removal of the a carboxy or amino protecting group are well known in the art. For example, an alkyl or cycloalkyl ester may be removed by basic hydrolysis, for instance an alkali metal hydroxide, such as sodium, potassium or lithium hydroxide in a suitable solvent, such as aqueous alcohol. A benzyl ester is typically removed by hydrogenation over a palladium catalyst. A basic nitrogen protected by a t-butyloxycarbonyl group, or a t-butyl ester, is typically removed by acid treatment, such as by trifluoroacetic acid or hydrochloric acid, optionally diluted with a solvent, such as methylene chloride and/or dioxane. The benzyloxycarbonyl group is generally removed by hydrogenation over a palladium catalyst. A trifluoroacetyl group is typically removed by basic hydrolysis, such as by treatment with an alkali metal hydroxide in a suitable solvent. One useful synthetic method for protecting the basic nitrogen of a piperidinyl group is to carry the group through a synthesis as a pyridinyl group, which may be reduced with a platinum catalyst toward the end of the synthesis to "remove" the protecting group.

Acid addition salts of the compounds are prepared in a standard manner in a suitable solvent from the parent compound and an excess of an acid, such as hydrochloric, hydrobromic, sulfuric, phosphoric, acetic, maleic, succinic or methanesulfonic. Most of the compounds form inner salts or zwitterions which may be acceptable. Cationic salts are prepared by treating the parent compound with an excess of an alkine reagent, such as a hydroxide, carbonate or alkoxide, containing the appropriate cation; or with an appropriate organic amine. Cations such as Li+, Na+, K+, Ca++, Mg++ and $NH_4$+ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds of this invention may be used in vitro to inhibit the aggregation of platelets in blood and blood products, e.g., for storage, or for ex vivo manipulations such as in diagnostic, therapeutic or research use.

This invention also provides a method of inhibiting platelet aggregation and clot formation in a mammal, especially a human, which comprises the internal administration of a compound of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. The compounds of this invention are also useful for preventing restenosis of an artery or vein in a mammal following angioplasty. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. These compounds are also believed to be useful for adjunct therapy following angioplasty. In addition, the compounds of this invention may be useful in a method for the prevention of metastatic conditions, the prevention or treatment of fungal or bacterial infection, inducing immunostimulation, treatment of sickle cell disease, and the prevention or treatment of diseases in which bone resorption is a factor, such as osteoporosis.

The compounds of this invention may also be favorably administered with other agents which inhibit platelet aggregation. For instance, the compounds of this invention may be administered with compounds of the class of cyclooxygenase inhibitors, thromboxane antagonists, thromboxane synthetase inhibitors, heparins, thrombin inhibitors, ADP receptor inhibitors/antagonists and ticlopidine. Examples of such agents are aspirin, warfarin and clopidogrel.

The peptide is administered either orally or parenterally to the patient, in a manner such that the concentration of drug in the plasma is sufficient to inhibit platelet aggregation, or other such indication. The pharmaceutical composition containing the peptide Is administered at a dose between about 0.2 to about 50 mg/kg in a manner consistent with the condition of the patient. For acute therapy, parenteral administration is preferred. For persistent states of hyperaggregabillty, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compound is administered one to four times daily at a level of about 0.4 to about 50 mg/kg to achieve a total daily dose of about 0.4 to about 200 mg/kg/day.

This invention further provides a method for inhibiting the reocclusion or restenosis of an artery or vein following fibrinolytic therapy, which comprises internal administration of a compound of formula (I) and a fibrinolytic agent. It has been found that administration of an compound in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound is administered just prior to, at the same time as, or just after parenteral administration of tPA or other fibrinolytic agent. It may prove desirable to continue treatment with the compound for a period of time well after reperfusion has been established to maximally inhibit post-therapy reocclusion. The effective dose of tPA, SK, UK or pUK may be from 0.5 to 5 mg/kg and the effective dose of the peptide may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the compound may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the inhibitor followed by an infusion of the fibrinolytic agent.

The pharmacological activity of the compounds of this invention is assessed by their ability to inhibit the binding of $^3$H-SK&F 107260, a known RGD-fibrinogen antagonist, to the GPIIbIIIa receptor; their ability to inhibit platelet aggregation, in vitro, and their ability to inhibit thrombus formation in vivo.

Inhibition of RGD-mediated GPIIb-IIIa binding

Inhibition of RGD-mediated GPIIb-IIIa binding was demonstrated by assessing the ability of compounds to inhibit the binding of $^3$H-SK&F 107260, a known RGD-fibrinogen antagonist, to the GPIIbIIIa receptor according to the procedure disclosed in WO 93/00095 (PCT/US/92/05463.

Inhibition of Platelet Aggregation

Inhibition of platelet aggregation was demonstrated following the procedure disclosed in WO 93/00095 (PCT/US/92/05463).

The compounds of this invention generally inhibit the aggregation of human platelets stimulated with ADP with IC50 of less than 0.1 uM. The compounds of Examples 7, 22, 23 and 26 have IC50 of between 0.2 and 11 uM, and the compound of Example 4 had an IC50 of about 75 uM. Preferred compounds have IC50 of less than 0.04 uM.

To assess the stability of the compounds to plasma proteases, the compounds were incubated for 3 h (rather than 3 min) in the PRP prior to addition of the agonist.

In Vivo Inhibition of Platelet Aggregation

In vivo inhibition of thrombus formation is demonstrated by recording the systemic and hemodynamic effects of infusion of the compounds into anesthetized dogs according to the methods described in Aiken et al., *Prostaglandins*, 19, 629 (1980). Alternately, inhibition of thrombus formation and bioavailability may be measured by the method disclosed by Nichols et al., J. Pharmacol. Exp. Ther., 270, 614 (1994).

The examples which follow are intended to in no way limit the scope of this invention, but are provided to illustrate how to make and use the compounds of this invention. Many other embodiments will be readily apparent and available to those skilled in the art.

EXAMPLES

In the Examples, all temperatures are in degrees Centigrade. Mass spectra were performed using fast atom bombardment (FAB) or electro-spray (ES) ionization. Melting points were taken on a Thomas-Hoover capillary melting point apparatus and are uncorrected.

NMR were recorded at 250 MHz using a Bruker AM 250 spectrometer, unless otherwise indicated. Chemical shifts are reported in ppm ($\delta$) downfield from tetramethylsilane. Multiplicities for NMR spectra are indicated as: s=singlet, d=doutblet, t=triplet, q=quartet, m=multiplet, dd=doublet of doublets, dt=doublet of triplets etc. and br indicates a broad signal. J indicates the NMR coupling constant in Hertz.

Celite® is filter aid composed of acid washed diatomaceous silica, and is a registered trademark of Mansville Corp., Denver, Colo. Florisil® is an activated magnesium silicate chromatographic support and is a registered trademark of Floridon Co., Pittsburgh, Pa. Analtech silica gel GF and EM silica gel thin layer plates were used for thin layer chromatography. Both flash and gravity chromatography were carried out on Merck 60 (230–400 mesh) silica gel. ODS refers to an octadecylsilyl derivatized silica gel chromatographic support. AN/W-TFA indicates an isocratic eluant system of the indicated percentage of acetonitrile in water with 0.1% TFA. 5μ Apex-ODS indicates an octadecylsilane derivatized silica gel support, having a nominal particle size of 5μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinyl benzene) chromatographic support and is a registered trademark of Hamilton Co., Reno, Nev.

Preparation 1

Preparation of N-methyl-2-[N-(benzyloxycarbonyl)-4-piperidinyl]ethanamine a) N-(tert-butoxycarbonyl)-N-methyl-2-(4-pyridyl)ethanamine A solution of N-methyl-2-(4-pyridyl)ethanamine (10 g, 74 mmol) in dichloromethane (250 mL) was stirred at 0° C., and treated with di-tert-butyl dicarbonate (16 g, 74 mmol) and triethylamine (10.2 mL, 74 mmol). The mixture was stirred for 24 h, diluted with chloroform and washed with 5% sodium bicarbonate. The organic phase was dried and concentrated to give the title compound.

b) N-(tert-butoxycarbonyl)-N-methyl-2-(4-piperidinyl)ethanamine

A solution of the compound of Preparation 1(a) (4.4 g, 18 mmol) in ethanol (30 mL) was cooled to 0° C., adjusted to pH 5 with 3N hydrochloric acid (6 mL), treated with platinum oxide (350 mg) and shaken with hydrogen for 2 h. The mixture was filtered through Celite® and the filtrate was treated with 10% sodium hydroxide (4 mL) and concentrated to give the title compound.

c) N-(tert-butoxycarbonyl)-N-methyl-2-[N-(benzyloxycarbonyl)-4-piperidinyl]ethanamine A mixture of the compound of Preparation 1(b) (4.4 g, 18 mmol) and triethylamine (2.5 mL, 18 mmol) in dimethylformamide (100 mL) was stirred at 0° C. and treated with N-(benzyloxycarbonyl)succinimide (4.4 g, 18 mmol). The mixture was stirred at RT for 15 h, concentrated, and the residue was chromatographed (silica gel, 80% ethyl acetate:hexane) to give the title compound (5.2 g, 77%).

d) N-methyl-2-[N-(benzyloxycarbonyl)-4-piperidinyl]ethanamine

A solution of the compound of Preparation 1(c) (2.2 g, 5.8 mmol) in dichloromethane (15 mL) was treated with TFA (5 mL) and stirred for 2.5 h. The mixture was diluted with chloroform, washed with 10% sodium hydroxide and the organic phase was washed, dried and concentrated. The residue was treated with toluene and concentrated to give the title compound.

Preparation 2

Preparation of 4-[N-(benzyloxycarbonyl)(aminoiminomethyl)]-3-fluoro-N-methyl-aniline a) 2-fluoro-4-(methylamino)benzonitrile To a solution of 2-fluoro-4-aminobenzonitrile [*Ind. Chim. Belg.*, 39, 490–500 (1974)] (3.8 g, 28 mmol) in anhydrous triethyl orthoformate (50 mL) was added trifluoroacetic acid (0.16 g, 1.4 mmol). The solution was heated to reflux 45 min, cooled and concentrated to give a yellow crystalline solid. To a solution of this solid in absolute ethanol (60 mL) at 0° C. was added sodium borohydride (3.2 g, 84 mmol). The resulting suspension was stirred at RT for 20 min, heated at reflux for 1 h, cooled and concentrated to give a colorless solid. This residue was partitioned between ether and water and the aqueous layer was extracted with ether. The organic phases were combined, washed with brine and dried (sodium sulfate). Concentration gave a white solid which was slurried in 35% ethyl acetate:hexane (200 mL) and filtered to give the title compound (3.7 g, 88%). mp 110–112° C.; $^1$H NMR (400 MHz, CDCl$_3$) δ 7.35 (m, 1H), 6.4 (dd, 1H), 6.3 (dd, 1H), 2.9 (s, 3H).

b) 2-fluoro-4-(methylamino)-[N-(benzyloxycarbonyl)]benzamidine

To a suspension of ammonium chloride (3.8 g, 72 mmol) in anhydrous toluene (40 mL) at 0° C. was added a solution of trimethylaluminum in toluene (2.0 M, 72 mmol) dropwise over 5 min. The solution was stirred at RT for 45 min. The compound of Preparation 2(a) (3.6 g, 24 mmol) was added in one portion and the resulting solution was heated at 80° C. for 22 h, cooled and poured onto a slurry of silica gel (120 g) and chloroform (350 mL). This slurry was stirred for 45 min, filtered and the filter cake was washed with methanol (700 mL). The filtrate was concentrated to a yellow solid which was dissolved in a mixture of THF and water. To this solution at 0° C., 5M sodium hydroxide (14 mL, 75 mmol) was added, followed by dropwise addition of benzyl chloroformate (4.1 g, 24 mmol) over 5 min. The cold solution was stirred for 30 min and concentrated. The resulting aqueous suspension was extracted with dichloromethane and then with ethyl acetate. The organic layers were combined, dried (sodium sulfate) and concentrated to give a yellow solid which was purified by chromatography (silica gel, 2% methanol:dichloromethane) to give the title compound as a white powder (2.6 g, 34%). mp 128–30° C. $^1$H NMR (400 MHz, CDCl$_3$) δ 8.2 (t, 1H), 7.5–7.25 (m, 5H), 6.4 (dd, 1H), 6.25 (dd, 1H), 5.2 (s, 2H), 4.6 (b, 1H), 2.8 (d, 3H).

Preparation 3

Preparation of N$^2$-(tert-butoxycarbonyl)-7-amino-1,2,3,4-tetrahydroisoquinoline a) 7-nitro-1,2,3,4-tetrahydro-isoquinoline.

To a mixture of 7-nitro-1,2,3,4-tetrahydroisoquinolinone (1.50 g, 7.8 mmol) in THF (15 mL) was added 2M borane methylsulfide in THF (9.0 mL, 18 mmol) dropwise. After addition was complete, the clear solution was heated to reflux for 4 h. The solution was s cooled to RT, and dry hydrogen chloride was bubbled into the solution to pH 2. The solution was heated to reflux for 1.5 h, cooled to 0° C. and diluted with ether. The resulting white solid was filtered and dried in vacuo to yield the title compound (1.62 g, 76%). MS(ES) m/e 179 [M+H]$^+$.

b) N$^2$-(t-butoxycarbonyl)-7-nitro-1,2,3,4-tetraydroisoquinoline

A solution of the compound of Preparation 3(a) (1.0 g, 5.6 mmol), di-tert-butyl dicarbonate (1.8 g, 8.4 mmol) and 4-(dimethylamino)pyridine (342 mg, 2.8 mmol) in dichloromethane (50 mL) was adjusted to pH 8.0 by the addition of triethylamine. After 4 h, the resulting solution was concentrated and the residue was taken up into ethyl acetate. The solution was extracted with 5% citric acid, brine, and dried (magnesium sulfate). The organic phase was diluted with hexane, filtered and the filtrate was dried in vacuo to give the title compound (1.41 g, 93%). MS(ES) m/e 279 [M+H]$^+$.

c) N$^2$-(tert-butoxycarbonyl)-7-amino-1,2,3,4-tetraydroisoquinoline

A mixture of the compound of Preparation 3(b) (1.41 g, 5.1 mmol) and Pd/BaSO$_4$ (100 mg) in methanol (25 mL) was shaken with hydrogen (45 psi) for 1.5 h. The mixture was filtered and the filtrate concentrated to yield the title compound (1.23 g, 90% overall). MS(ES) m/e 249 [M+H]$^+$.

Preparation 4

Preparation of N-(tert-butoxycarbonyl)-2-(4-piperidinyl)ethanamine

Using the procedure of Preparation 1(a)–(b), except substituting 2-(4-pyridyl)ethanamine for N-methyl-2-(4-pyridyl)ethanamine gave the title compound.

Preparation 5

Preparation of (5-iodopentyl)benzene a) [5-(methanesulfonyloxy)pentyl)]benzene Methanesulfonyl chloride (4.3 mL, 55 mmol) was added dropwise over 2 min to a solution of 5-phenylpentanol (8.4 mL, 50 mmol) and dry triethylamine (14 mL, 100 mmol) in anhydrous dichloromethane (100 mL) at 0° C. under argon. After 45 min, the reaction was diluted with ether and washed sequentially with cold 1N hydrochloric acid, water, and brine. The organic phase was dried (MgSO$_4$) and concentrated to give the title compound (12.09 g, 100%) as a pale yellow oil, which was used without further purification. $^1$H NMR (250, CDCl$_3$) δ 7.10–7.35 (m, 5H), 4.22 (t, J=6.5 Hz, 2H), 2.98 (s, 3H), 2.63 (t, J=7.6 Hz, 2H), 1.37–1.85 (m, 6H).

b) (5-iodopentyl)benzene

A solution of the compound of Preparation 5(a) (12.09 g, 50 mmol) and sodium iodide (8.99 g, 60 mmol) in acetone (250 mL) was heated at reflux. After 3 h, the reaction was cooled and filtered through a glass frit, and the filtrate was concentrated. The residue was dissolved in ether and washed with 1N sodium thiosulfate. The organic phase was dried (MgSO$_4$), concentrated, and chromatographed (silica gel, hexane) to give the title compound (11.5 g, 84%) as a colorless oil. $^1$H NMR (250, CDCl$_3$) δ 7.05–7.40 (m, 5H), 3.18 (t, J=7.0 Hz, 2H), 2.62 (t, J=7.6 Hz, 2H), 1.79–1.93 (m, 2H), 1.37–1.72 (m, 4H); IR (CCl$_4$) 3020, 2930, 2850, 1495, 1451, 1200 cm$^{-1}$; MS (DCI/NH$_3$) m/e 292.1 [M+NH$_4$]$^+$.

Preparation 6

Preparation of N-methyl-3-[N-(tert-butoxycarbonyl)piperidin-4-yl]propanamine The compound of Preparation 6(a) (2.0 g, 8.3 mmol) was dissolved in dichloromethane (25 mL), treated with triethylamine (0.86 g, 8.6 mmol) and stirred at 0° C. The resulting mixture was treated with triflic anhydride (2.5 g, 8.9 mmol), stirred for 30 min at 0° C. and slowly added to a solution of methylamine in dichloromethane at 0° C. The mixture was stirred and allowed to warm to RT for 1 h. The mixture was concentrated and the residue was flash chromatographed (silica gel, 5–20% methanol:chloroform) to give the title compound (2.8 g). MS(ES) m/e 257 [M+H$^+$.

Preparation 7

Preparation of (R,S)-[7-[[4-(aminoiminomethyl)phenyl]amino]carbonyl]-4-(2-phenylethyl)-1,3,4,5-tetrahydro-3-oxo-2H-1,4-benzodiazepine-2-acetic acid a) t-butyl 3-methyl-4-nitro-benzoate Benzenesulfonyl chloride (12.8 mL, 100 mmol) was added rapidly to a solution of 3-methyl-4-nitrobenzoic acid (9.06 g, 50 mmol) in dry pyridine (25 mL) at 40° C. The reaction was mildly exothermic. The cloudy, orange solution was stirred for 5 min, then t-butanol (4.7 mL, 50 mmol, 1 eq.) was added. After 1 h, the reddish-orange mixture was poured into ice/water (200 mL), and the resulting mixture was stirred briskly for 1 h. The solid was collected by suction filtration, washed with H$_2$O, and dissolved in toluene (200 mL). The solution was dried (MgSO$_4$) and filtered through a pad of silica gel eluting with toluene. Concentration gave the title compound as a yellow oil which crystallized under vacuum (9.67 g, 82%).

b) t-butyl 4-nitro-3-[N-(2-phenylethyl)aminomethyl]benzoate

A mixture of the compound of Preparation 7(a) (4.75 g, 20 mmol), N-bromosuccinimide (3.92 g, 22 mmol), and benzoyl peroxide (0.24 g, 1 mmol) in CCl$_4$ (50 mL) was heated at reflux. After 16 h, the mixture was filtered to remove the succinimide, and the filtrate was concentrated to a yellow oil. The benzyl bromide was used without purification. The crude benzyl bromide obtained above was dissolved in dry THF (50 mL), and solid NaHCO$_3$ (2.52 g, 30 mmol) was added. The mixture was stirred briskly, and phenethylamine (3.8 mL, 30 mmol) was added. The color of the solution darkened slightly to a deeper yellow. Within several min, the mixture had become very cloudy. After 4 h, the reaction was concentrated and the residue was partitioned between H$_2$O (50 mL) and Et$_2$O (100 mL). Separation of the phases, extraction with Et$_2$O, drying (MgSO$_4$), and concentration gave a yellow oil. Chromatography (silica gel, 20% EtOAc/hexane) gave the title compound (2.86 g, 40%) as a yellow oil.

c) t-butyl 4-nitro-3-[N-(t-butyloxycarbonyl)-N-(2-phenylethyl)aminomethyl]benzoate Di-t-butyl dicarbonate (2.10 g, 9.62 mmol) was added all at once to a solution of the compound of Preparation 7(b) (2.86 g, 8.02 mmol) in CHCl$_3$ (30 mL) at room temperature. The reaction was stirred at room temperature for 2.5 h, then at reflux for 0.5 h. Concentration and chromatography (silica gel, 15% EtOAc/hexane) gave the title compound (3.70 g,) as a yellow oil.

d) t-butyl 4-amino-3-[N-(t-butyloxycarbonyl)-N-(2-phenylethyl)aminomethyl]benzoate A mixture of the compound of Preparation 7(c) (2.66 g, 5.83 mmol), 10% Pd/C (0.62 g, 0.58 mmol Pd), and EtOAc (60 mL) was shaken under H$_2$ (50 psi). After 3 h, the mixture was filtered to remove the catalyst, and the filtrate was concentrated to dryness. Chromatography (silica gel, 20% EtOAc/hexane) gave the title compound as a yellow foamy oil which slowly partially solidified (2.26 g, 91%).

e) t-butyl (R,S)-4-[2-(1,4-dimethoxy-1,4-dioxo-2-butyl)-amino]-3-[N-(t-butyloxycarbonyl)-N-(2-phenylethyl)-aminomethyl]-benzoate A mixture of the compound of Preparation 7(d) (1.98 g, 4.64 mmol), dimethylacetylene dicarboxylate (1.14 mL, 9.28 mmol), and MeOH (9.3 mL) was heated to reflux under argon. A homogeneous solution resulted. After 1 h, the solution was concentrated to a yellow oil. Chromatography (silica gel, 1:1 EtOAc:hexane) gave a yellow oil. This was used without further purification. TLC R$_f$ 0.61 (major product), R$_f$ 0.41 (minor product) (30% EtOAc/hexane).

The yellow oil obtained above was dissolved in EtOAc (93 mL), and 10% Pd/C (1.48 g, 1.39 mmol Pd, 0.3 eq.) was added. The mixture was shaken at RT under H$_2$ (45 psi) for 5 h, then was filtered to remove the catalyst. Concentration of the filtrate gave a colorless oil which was chromatographed (silica gel, 20% EtOAc/hexane) to afford the title compound as a colorless oil (2.49 g, 94%).

f) methyl (R,S)-7-carboxy-4-(2-phenylethyl)-1,3,4,5-tetrahydro-3-oxo-2H-1,4-benzodiazepine-2-acetic acid TFA (9 mL) was added all at once to a solution of the compound of Preparation 7(e) (2.11 g, 3.70 mmol) in dry CH$_2$Cl$_2$ (9 mL) at 0° C. under argon. The resulting light yellow solution was warmed to room temperature, stirred for 2 h, and concentrated. The residue was dissolved and reconcentrated from toluene to remove residual TFA. The resultant light yellow oil was dissolved in anhydrous MeOH (18.5 mL), and the solution was cooled to 0° C. under argon. Freshly prepared NaOMe/MeOH (1.0M; 18.5 mL, 18.5 mmol) was added dropwise over 5 min. The ice bath was removed, the yellow solution was allowed to warm to room temperature over 10 min, and was heated to reflux under argon. After 1.5 h, the reaction was cooled in ice and quenched with glacial acetic acid (2.1 mL, 37 mmol). The mixture was concentrated and the residue was partitioned between EtOAc (50 mL) and $H_2O$ (50 mL). The layers were separated and the aqueous layer was extracted exhaustively with EtOAc (in 50 mL portions) until all solids had dissolved. The combined organic layers were dried ($MgSO_4$) and concentrated until crystallization was initiated. The resulting mixture was cooled thoroughly in ice. Suction filtration afforded the title compound as colorless crystals (1.0 g, 71%). The mother liquors were concentrated and the residue was chromatographed (silica gel, 10% MeOH/ $CHCl_3$-trace acetic acid) to afford additional crude material. Recrystallization from EtOAc containing a little MeOH yielded an additional amount of the pure title compound (1.23 g, 87%, total isolated yield).

g) methyl (R,S)-[7-[[4-[N-(benzyloxycarbonyl)amino-iminomethyl)]phenyl]amino]carbonyl]-1,3,4,5-tetrahydro-3-oxo-4-(2-phenylethyl)-2H-1,4-benzodiazepine-2-acetate The compound of Preparation 7(f) (95.6 mg, 0.25 mmol) was refluxed with $SOCl_2$ (2.5 mL) for 15 min, and the yellow solution was concentrated to dryness. The yellow oily solid was dissolved in dry $CH_2Cl_2$ (2.5 mL), and 4-[N-(benzyloxycarbonyl)aminoimino-methyl]aniline (134.7 mg, 0.5 mmol) was added. The mixture was cooled in ice/$H_2O$ under argon, and anhydrous pyridine (0.061 mL, 0.75 mmol) was added dropwise. The resulting orangish-yellow mixture was warmed to room temperature. After 1.5 h, the reaction was quenched with 5% $NaHCO_3$ (5 mL) and extracted thoroughly with EtOAc. Drying ($Na_2SO_4$), concentration, chromatography (silica gel, 3:2 EtOAc:$CHCl_3$-0.5% MeOH), and preparative TLC of mixed fractions from the chromatography (same solvent system) gave the title compound as a pale yellow oil (110.2 mg, 70%).

h) (R,S)-[7-[[4-(aminoiminomethyl)phenyl]amino] carbonyl]-4-(2-phenylethyl)-1,3,4,5-tetrahydro-3-oxo-2H-1,4-benzodiazepine-2-acetic acid A solution of the compound of Preparation 7(g) (87.0 mg, 0.1373 mmol) in 1:1 EtOAc:MeOH (4.6 mL) containing 10% Pd/C (29.2 mg, 0.0275 mmol) and TFA (0.011 mL, 0.137 mmol) was stirred briskly under $H_2$. After 1 h, the mixture was filtered to remove the catalyst, and the filter pad was washed thoroughly with EtOAc and EtOAc/MeOH. Concentration of the solution provided a yellow, oily solid (83.0 mg). This was dissolved in MeOH (4.6 mL), and 1.0N NaOH (0.41 mL, 0.41 mmol) was added. The light yellow solution was stirred at room temperature overnight, cooled to 0° C., and acidified with TFA (0.106 mL, 1.373 mmol). The solution was concentrated to dryness to provide an orangish-yellow oil. This material was purified by preparative HPLC (PRP-1®, gradient, A:5% $CH_3CN/H_2O$-0.1% TFA) for 5 min, increased to B:23% $CH_3CN/H_2O$-0.1% TFA, A for 5 min, A to B during 24 min). The fractions containing the pure product were combined and concentrated until precipitation occurred. The solid was dissolved by addition of a minimum of $CH_3CN$, and the solution was lyophillized to give the title compound as a faintly yellow powder (50%).

Preparation 8

Preparation of (R,S)-7-[[[4-(aminoiminomethyl) phenyl]-methylamino]carbonyl]-2,3,4,5-tetrahydro-3-oxo-2-(2-phenylethyl)-1H-2-benzazepine-4-acetic acid a) t-butyl 3-bromo-4-methylbenzoate Dimethylformamide dimethyl acetal (48 mL, 200 mmol) was added dropwise over 15 min to a suspension of 3-bromo-4-methylbenzoic acid (85%; 10.75 g, 42.5 mmol) in toluene (100 mL) at 70° C. The reaction was stirred at 70–80° C. for an additional 0.5 h, then was cooled, washed sequentially with water and 5% sodium bicarbonate, and dried (sodium sulfate). The mixture was filtered through a pad of silica gel, and the filter pad was washed with toluene. The filtrate was concentrated to afford the title compound (8.0 g, 69%) as a yellow oil. TLC (toluene) $R_f$ 0.68.

b) t-butyl 3-bromo-4-(bromomethyl)benzoate

A mixture of the compound of Preparation 8(a) (1.36 g, 5 mmol), N-bromosuccinimide (0.98 g, 5.5 mmol), and benzoyl peroxide (61 mg, 0.25 mmol) in carbon tetrachloride (25 mL) was heated at reflux. After 4 h, the mixture was cooled and filtered, and the filtrate was concentrated. The resulting material was used without purification. TLC $R_f$ 0.39 (5:95 ethyl acetate:hexane).

c) t-butyl 3-bromo-4-[[(2-phenylethyl)amino]methyl]-benzoate

The compound of Preparation 8(b) was dissolved in dry ether (25 mL), and phenethylamine (1.9 mL, 15 mmol) was added. The addition was slightly exothermic, and the reaction became cloudy. The reaction was stirred at RT overnight, then was diluted with ether (75 mL) and was washed sequentially with 5% sodium bicarbonate and brine (25 mL). Drying ($MgSO_4$), concentration, and silica gel chromatography (33% ethyl acetate/hexane) gave the title compound (1.26 g, 65%) as a pale yellow oil. TIC $R_f$ 0.42 (30:70 ethyl acetate:hexane).

d) t-butyl 3-bromo-4-[[[N-(2-phenylethyl)-N-t-butoxycarbonyl]amino]methyl]benzoate Di-t-butyl dicarbonate (845 mg, 3.88 mmol) was added all at once to a solution of the compound of Preparation 8(c) (1.26 g, 3.23 mmol) in chloroform (16 mL) at RT. The reaction was stirred at RT for 1.5 h, then at reflux for 0.5 h. Concentration and chromatography (silica gel, 10% ethyl acetate/hexane) gave the title compound (1.57 g, 99%) as a colorless oil which solidified in vacuo. TLC $R_f$ 0.49 (10:90 ethyl acetate:hexane).

e) methyl 3-methoxycarbonyl-4-[[5-(t-butoxycarbonyl)-2-[[N-(2-phenylethyl)-N-t-(butoxycarbonyl)]amino]methyl]-phenyl]-2-butenoate and methyl 3-methoxycarbonyl-4-[[5-(t-butoxycarbonyl)-2-[[N-(2-phenylethyl)-N-t-butoxycarbonyl)]amino]methyl]phenyl]-3-butenoate.

A mixture of the compound of Preparation 8(d) (1.34 g, 2.73 mmol), dimethyl itaconate (648 mg, 4.10 mmol), palladium (II) acetate (30.7 mg, 0.14 mmol), tri-o-tolylphosphine (83.2 mg, 0.27 mmol), dry triethylamine (0.76 mL, 5.46 mmol), and dry acetonitrile (27 mL) was deoxygenated through a single evacuation/argon purge cycle, then was heated at reflux under argon. After 6 h, the reaction was cooled, and more palladium (II) acetate (30.7 mg, 0.14 mmol) and tri-o-tolylphosphine (83.2 mg, 0.27 mmol) were added. The mixture was deoxygenated through three evacuation/argon purge cycles, then was heated at reflux under argon overnight (16.5 h). The reaction was concentrated, and the residue was dissolved in ether and washed with water and brine. Drying ($MgSO_4$), concentration, and chromatography (silica gel, 15% ethyl acetate/hexane; then 40% ethyl acetate/hexane) gave the crude title compound as a yellow oil. The residue was rechromatographed (silica gel, 25% ethyl acetate/hexane) to yield the title compound (1.36 g, 88%) as a light yellow oil. This material was used without separation of the isomeric reaction products.

f) methyl 3-methoxycarbonyl-4-[5-(t-butoxycarbonyl)-2-[[[N-(2-phenylethyl)-N-t-butoxycarbonyl]amino]methyl]-phenyl]butanoate The compound of Preparation 8(e) (1.18 g, 2.08 mmol) was dissolved in anhydrous methanol (21 mL), and palladium (II) hydroxide on carbon (0.21 g) was added. The resulting mixture was shaken at RT under $H_2$ (47 psi) for 2 h, then was filtered through Celite®. The filtrate was concentrated and resubmitted to the same reaction conditions. After another 5.5 h, the mixture was filtered as before, and the filtrate was concentrated to afford the title compound (1.13 g, 95%) as a colorless oil.

g) methyl (R,S)-7-carboxy-2,3,4,5-tetrahydro-3-oxo-2-(2-phenylethyl)-1H-2-benzazepine-4-acetate TFA (11 mL) was added all at once to a cloudy solution of the compound of Preparation 8(f) (1.30 g, 2.28 mmol) in dry $CH_2Cl_2$ (11 mL) at 0° C. under argon. The resulting light yellow solution was warmed to RT, stirred for 2 h, and concentrated. The residue was concentrated once from 1,2-dichloroethane to remove residual TFA and give methyl 3-methoxycarbonyl-4-[5-carboxy-2-[[N-(2-phenylethyl)amino]methyl]phenyl]butanoate as a pale green oil.

The oil was dissolved in anhydrous methanol (11 mL), and the solution was cooled to 0° C. under argon. Freshly prepared 1.0 M sodium methoxide/methanol (11 mL, 11 mmol) was added and the ice bath was removed. The yellow solution was allowed to warm to RT over 5 min and heated to reflux under argon. After 3 h, the reaction was cooled in ice and quenched with glacial acetic acid (1.3 mL, 22.8 mmol). The reaction was diluted with ethyl acetate (100 mL) and washed with water. The combined aqueous layers were back-extracted with ethyl acetate, and the combined ethyl acetate layers were washed with brine, dried ($MgSO_4$), and concentrated to a pale green residue. Chromatography ((silica gel, 10% methanol/chloroform/0.1% acetic acid) gave the title compound as a yellow foam. Crystallization from methanol containing a little chloroform gave the title compound (528.2 mg, 61%) as an off-white solid. mp 214–216° C.; TLC $R_f$ 0.49 (10:90 methanol:chloroform).

h) methyl (R,S)-7-[[[4-[N-(benzyloxycarbonyl)-aminoiminomethyl]phenyl]methylamino]carbonyl]-2,3,4,5-tetrahydro-3-oxo-2-(2-phenylethyl)-1H-2-benzazepine-4-acetate The compound of Preparation 8(g) (117.9 mg, 0.31 mmol) was refluxed with thionyl chloride (3 mL) for 15 min and the yellow solution was concentrated. The residue was concentrated from dry toluene (3 mL) to remove residual thionyl chloride, and the resulting material was dissolved in dry $CH_2Cl_2$ (0.5 mL). This solution was added dropwise over 1–2 min to a solution of 4-(methylamino)-(N-benzyloxycarbonyl)benzamidine (263 mg, 0.93 mmol) and anhydrous pyridine (0.125 mL, 1.55 mmol) in dry $CH_2Cl_2$ (10 mL) at 0° C. under argon. The resulting yellow mixture was warmed to RT and stirred for 0.5 h, diluted with ethyl acetate, and washed with 5% sodium bicarbonate. Drying (sodium sulfate), concentration, and chromatography (silica gel, 10% ethyl acetate/toluene) gave the title compound (174.8 mg, 87%) as a faintly yellow oil. TLC $R_f$ 0.45 (9:1 toluene:ethyl acetate).

i) methyl (R,S)-7-[[[4-(aminoiminomethyl)phenyl]methylamino]carbonyl]-2,3,4,5-tetrahydro-3-oxo-2-(2-phenylethyl)-1H-2-benzazepine-4-acetate 10% Palladium on carbon (58 mg, 0.054 mmol) was added carefully to a solution of the compound of Preparation 8(h) (174.8 mg, 0.27 mmol) and TFA (0.021 mL, 0.27 mmol) in ethyl acetate/methanol (1:1, 9 mL), and the mixture was stirred briskly under hydrogen (balloon pressure). After 1.5 h, the mixture was filtered through Celite®, and the filter pad was washed thoroughly with ethyl acetate and methanol. Concentration gave the title compound.

j) (R,S)-7-[[[4-(aminoiminomethyl)phenyl]methylamino]carbonyl]-2,3,4,5-tetrahydro-3-oxo-2-(2-phenylethyl)-1H-2-benzazepine-4-acetic acid The compound of Preparation 8(i) was dissolved in methanol (9 mL), and 1.0 N sodium hydroxide (0.81 mL, 0.81 mmol) was added. The solution was stirred at RT overnight, then was concentrated. The residue was dissolved in water/acetonitrile (3 mL), cooled to 0° C., and acidified with TFA (0.21 mL, 2.7 mmol). The faintly yellow solution was concentrated and the residue was purified by reversed-phase flash chromatography (C-18 silica gel, 25% AN/W-TFA). Concentration and lyophilization gave the title compound (123 mg, 67%) as a colorless powder.

The following Examples illustrate the manner of making the pharmacologically active compounds and compositions of this invention.

Example 1

Preparation of (R,S)-2,3,4,5-tetrahydro-4-methyl-3-oxo-8-[[[2-(4-piperidinyl)ethyl]methylamino]carbonyl]-1H-1,4-benzodiazepine-2-acetic acid a) methyl (R,S)-8-[[[2-[N-(benzyloxycarbonyl)-4-piperidinyl]ethyl]methylamino]carbonyl]-2,3,4,5-tetrahydro-4-methyl-3-oxo-1H-1,4-benzodiazepine-2-acetate Methyl (R,S)-8-carboxy-2,3,4,5-tetrahydro-4-methyl-3-oxo-1H-1,4-benzodiazepine-2-acetate (2.0 mmol) dissolved in DMF (30 mL) was treated with EDC (2.2 mmol), 1-HOBT (285 mg, 2.1 mmol) and adjusted to pH 7 with triethylamine. The mixture was treated with N-methyl-2-[N-(benzyloxycarbonyl)-4-piperidinyl]ethanamine (2.4 mmol), stirred at RT for 48 h, concentrated and the residue was purified by flash chromatography to yield the title compound. $^1$H NMR (DMSO-$d_6$) δ 6.5–7.5 (m, 7H), 2.6–4.1 (m, 24H), 0.9–1.8 (m, 7H); MS(ES) m/e 551 [M+H]$^+$, [M+HCO$_3^-$]$^-$ 595.

b) methyl (R,S)-2,3,4,5-tetrahydro-4-methyl-3-oxo-8-[[[2-(4-piperidinyl)ethyl]methylamino]carbonyl]-1H-1,4-benzodiazepine-2-acetate A solution of the compound of Example 1(a) (0.06 mmol) in methanol (25 mL) containing 1.0M hydrogen chloride in ether (0.6 mL) was treated with 10% palladium hydroxide and the mixture was shaken in a hydrogen atmosphere (40 psi) for 1 h. The mixture was filtered and concentrated to yield the title compound. MS(ES) m/e 417 [M+H]$^+$.

c) (R,S)-2,3,4,5-tetrahydro-4-methyl-3-oxo-8-[[[2-(4-piperidinyl)ethyl]methylamino]carbonyl]-1H-1,4-benzodiazepine-2-acetic acid The compound of Example 1(b) (0.26 mmol) was dissolved in methanol (9 mL), and 1.0 N sodium hydroxide (0.81 mL, 0.81 mmol) was added. The solution was stirred at RT overnight, and concentrated. The residue was dissolved in water/acetonitrile (3 mL), cooled to 0° C., and acidified with TFA (0.21 mL, 2.7 mmol). The solution was concentrated and the residue was purified by reversed-phase flash chromatography (C-18 silica gel, AN/W-TFA). Concentration and lyophilization gave the title compound. MS(ES) m/e 403 [M+H]$^+$; $^1$H NMR (DMSO-$d_6$) δ 8.1–8.6

(m, 2H), 6.4–7.0 (m, 3H), 5.9–6.0 (m, 1H), 5.4–5.5 (d, 1H), 5.0–5.1 (m, 1H), 3.8–3.9 (d, 1H), 1.0–3.5 (m, 22H); Anal. ($C_{24}H_{35.25}N_4O_{8.875}$) calcd: C, 48.91; H, 5.71; N, 9.51. found: C, 49.19; H, 5.64; N, 9.42.

Example 2

Preparation of (R,S)-2,3,4,5-tetrahydro-4-isopentyl-3-oxo-8-[[[2-(4-piperidinyl)ethyl]methylamino]carbonyl]-1H-1,4-benzodiazepine-2-acetic acid a) methyl (R,S)-8-carboxy-2,3,4,5-tetrahydro-4-isopentyl-3-oxo-1H-1,4-benzodiazepine-2-acetate Anhydrous isopentylamine was bubbled into anhydrous DMF (200 mL) at 0° C. for 15 min. A solution of t-butyl 4-bromomethyl-3-nitrobenzoate (5.0 g, 15.8 mmol) (*Int. J. Peptide. Res.*, 36, 31 (1990)) in DMF (10 mL) was added dropwise to the cold amine solution. The solution was stirred at 0° for 30 min and poured into water. The mixture was extracted with ethyl acetate and the combined organic layers were washed with water, dried (sodium sulfate) and concentrated to give a yellow-brown oil. The oil was purified by chromatography over silica gel to yield t-butyl 4-(isopentylamino)methyl-3-nitrobenzoate.

A solution of the t-butyl 4-(isopentylamino)methyl-3-nitrobenzoate (5.3 mmol), triethylamine (2.1 g, 21 mmol) and di-t-butyl dicarbonate (3.44 g, 15.8 mmol) in THF (50 mL) was stirred 24 h. The mixture was concentrated and the residue dissolved in ethyl acetate (200 mL). The solution was extracted with water, dried (sodium sulfate) and concentrated to give a yellow oil which was purified by chromatography over silica gel to yield t-butyl 4-[N-(t-butoxycarbonyl)-N-(isopentyl)amino-methyl]-3-nitrobenzoate.

A solution of t-butyl 4-[N-(t-butoxycarbonyl)-N-(isopentyl)amino-methyl]-3-nitrobenzoate (2.27 mmol) in ethanol (100 mL) containing 10% palladium on carbon (0.5 g) was hydrogenated (40 psi). After 30 min, the mixture was filtered and concentrated to give t-butyl 3-amino-4-[N-(t-butoxycarbonyl)-N-(isopentyl)-aminomethyl]benzoate.

Dimethyl acetylenedicarboxylate (0.34 g, 2.4 mmol) was added to a solution of t-butyl 3-amino-4-[N-(t-butoxycarbonyl)-N-(isopentyl)-aminomethyl]benzoate (2.7 mmol) in methanol (50 mL). The solution was heated to reflux for 1 h, treated with dimethyl acetylenedicarboxylate (0.17 g, 1.2 mmol) and heated at reflux for an additional 1 h. The mixture was cooled, filtered, concentrated and the residual yellow oil was chromatographed over ilica gel to give t-butyl (E,Z)-4-[N-(t-butoxycarbonyl)-N-(isopentyl)-aminomethyl]-3-[2-(1,4-dimethoxy-1,4-dioxo-2-butenyl)amino]-benzoate.

A solution of t-butyl (E,Z)-4-[N-(t-butoxycarbonyl)-N-(methyl)-aminomethyl]-3-[2-(1,4-dimethoxy-1,4-dioxo-2-butenyl)amino]-benzoate in methanol (50 mL) containing 10% Pd/carbon (0.5 g) was hydrogenated (45 psi) at RT. After 4 h, the suspension was filtered and concentrated to give a pale yellow oil. The residue was purified by chromatography over silica gel to yield t-butyl 4-[N-(t-butoxycarbonyl)-N-(isopentyl)amino-methyl]-3-[2-(1,4-dimethoxy-1,4-dioxo-2-butyl)amino]benzoate.

TFA (50 mL) was added to a solution of t-butyl 4-[N-(t-butoxycarbonyl)-N-(isopentyl)amino-methyl]-3-[2-(1,4-dimethoxy-1,4-dioxo-2-butyl)amino]benzoate (0.3 mmol) in $CH_2Cl_2$ (10 mL). The mixture was stirred for 4 h and concentrated to yield 4-[N-(isopentyl)aminomethyl]-3-[N-[2-(1,4-dimethoxy-1,4-dioxo-2-butyl)]-N-(methyl)amino]-benzoic acid.

The benzoic acid was dissolved in methanol (20 mL) and treated with 25% sodium methoxide in methanol (0.2 mL, 0.87 mmol). The mixture was heated to 50° C. for 2 h, cooled and treated with 1M hydrogen chloride in ether (2 mL). The mixture was concentrated to give the title compound b) methyl (R,S)-2,3,4,5-tetrahydro-4-isopentyl-3-oxo-8-[[[2-(4-pyridyl)ethyl]methylamino]carbonyl]-1H-1,4-benzodiazepine-2-acetate The compound of Example 2(a) (2.0 mmol) dissolved in DMF (30 mL) was treated with EDC (2.2 mmol) and 1-HOBT (285 mg, 2.1 mmol). The mixture was treated with N-methyl-2-(4-pyridyl)ethanamine (2.4 mmol), stirred at RT for 48 h, concentrated and the residue was purified by flash chromatography to yield the title compound.

c) methyl (R,S)-2,3,4,5-tetrahydro-4-isopentyl-3-oxo-8-[[[2-(4-piperidinyl)ethyl]methylamino]carbonyl]-1H-1,4-benzodiazepine-2-acetate A solution of the compound of Example 2(b) (0.2 mmol) and 0.6N hydrochloric acid (0.6 mL) in methanol (30 mL) was treated with platinum oxide (5 mg) and hydrogenated (45 psi) overnight. The mixture was filtered and concentrated to give the title compound. MS(ES) m/e 473 [M+H]$^+$.

d) (R,S)-2,3,4,5-tetrahydro-4-isopentyl-3-oxo-8-[[[2-(4-piperidinyl)ethyl]methylamino]carbonyl]-1H-1,4-benzodiazepine-2-acetic acid The compound of Example 2(c) (0.27 mmol) was dissolved in methanol (9 mL), and 1.0 N sodium hydroxide (0.81 mL, 0.81 mmol) was added. The solution was stirred at RT overnight, then was concentrated. The residue was dissolved in water/acetonitrile (3 mL), cooled to 0° C., and acidified with TFA (0.21 mL, 2.7 mmol). The solution was concentrated and the residue was purified by reversed-phase flash chromatography to yield the title compound. MS(ES) m/e 459 [M+H]$^+$.

Example 3

Preparation of (R,S)-8-[[[4-(aminoiminomethyl)-3-fluorophenyl]methylamino]carbonyl]-2,3,4,5-tetrahydro-3-oxo-4-(2-phenylethyl)-1H-1,4-benzodiazepine-2-acetic acid a) methyl (R,S)-8-[[[4-[N-(benzyloxycarbonyl)aminoiminomethyl]-3-fluorophenyl]methylamino]carbonyl]-2,3,4,5-tetra-hydro-3-oxo-4-(2-phenylethyl)-1H-1,4-benzodiazepine-2-acetate Using the procedure of Preparation 8(h), except substituting methyl (R,S)-8-carboxy-2,3,4,5-tetrahydro-3-oxo-4-(2-phenylethyl)-1H-1,4-benzodiazepine-2-acetate for the compound of Preparation 8(g), and substituting 2-fluoro-4-(methylamino)-[N-(benzyloxycarbonyl)]benzamidine for 4-(methylamino)-(N-benzyloxycarbonyl)benzamidine, gave the title compound. $^1$H NMR (400 MHz, CDCl$_3$) δ 8.15 (t, 1H), 7.4 (d, 2H), 7.4–7.15 (m, 8H), 7.1 (d, 2H), 6.9 (dd, 1H), 6.75 (dd, 1H), 6.65 (s, 1H), 6.6 (d, 1H), 6.4 (d, 1H), 5.25 (d, 1H), 5.15 (s, 2H), 4.9 (q, 1H), 4.25 (d, 1H), 3.7 (s, 3H), 3.65 (m, 2H), 3.55 (d, 1H), 3.45 (s, 3H), 2.95 (dd, 1H), 2.7 (m, 2H), 2.6 (dd, 1H).

b) (R,S)-8-[[[4-(aminoiminomethyl)-3-fluorophenyl]methyl-amino]carbonyl]-2,3,4,5-tetrahydro-3-oxo-4-(2-phenylethyl)-1H-1,4-benzodiazepine-2-acetic acid A solution of the compound of Example 3(a) (0.06 mmol) in methanol (25 mL) containing 1.0M hydrogen chloride in ether (0.6 mL) was treated with 10% palladium on carbon (0.06 g) and the mixture was shaken in a hydrogen atmosphere (40 psi) for 1 h. The mixture was filtered and concentrated to yield the methyl ester of the title compound.

The methyl ester (0.27 mmol) was dissolved in methanol (9 mL), and 1.0 N sodium hydroxide (0.81 mL, 0.81 mmol) was added. The solution was stirred at RT overnight, then was concentrated. The residue was dissolved in water/acetonitrile (3 mL), cooled to 0° C., and acidified with TFA (0.21 mL, 2.7 mmol). The solution was concentrated and the residue was purified by reversed-phase flash chromatography to yield the title compound. $^1$H NMR (400 MHz, CD$_3$OD) δ 7.75 (t, 1H), 7.4 (d, 1H), 7.25–7.05 (m, 6H), 6.8 (d, 1H), 6.7 (s, 1H), 6.5 (d, 1H), 5.35 (d, 1H), 5.05 (m, 1H), 3.8 (d, 1H), 3.65 (m, 2H), 3.4 (s, 3H), 2.9 (dd, 1H), 2.7 (m, 2H), 2.6 (dd, 1H). MS(ES) m/e 518.0 [M+H]$^+$.

Example 4

Preparation of (R,S)-8-[[(1,2,3,4-tetrahydro-7-isoquinolinyl]amino]carbonyl]-2,3,4,5-tetrahydro-3-oxo-4-(2-phenylethyl)-1H-1,4-benzodiazepine-2-acetic acid a) methyl (R,S)-8-[[N-(t-butoxycarbonyl)-1,2,3,4-tetrahydro-7-isoquinolinyl]amino]carbonyl]-2,3,4,5-tetrahydro-3-oxo-4-(2-phenylethyl)-1H-1,4-benzodiazepine-2-acetic acid Methyl (R,S)-8-carboxy-1,2,4,5-tetrahydro-3-oxo-4-(2-phenylethyl)-3H-1,4-benzodiazepine-2-acetate (2.0 mmol) dissolved in DMF (30 mL) was treated with EDC (2.2 mmol) and 1-HOBT (285 mg, 2.1 mmol). The mixture was treated with N$^2$-(tert-butoxycarbonyl)-7-amino-1,2,3,4-tetrahydro-isoquinoline (2.4 mmol), stirred at RT for 48 h, concentrated and the residue was purified by flash chromatography to yield the title compound.

b) (R,S)-8-[[(1,2,3,4-tetrahydro-7-isoquinolinyl]amino]-carbonyl]-2,3,4,5-tetraydro-3-oxo-4-(2-phenylethyl)-1H-1,4-benzodiazepine-2-acetic acid The compound of Example 4(a) (0.56 mmol) was dissolved in a mixture of CH$_2$Cl$_2$ (25 mL) and TFA (5 mL). After 1 h, the mixture was concentrated to give the methyl ester of the title compound.

The methyl ester (0.27 mmol) was dissolved in methanol (9 mL), and 1.0 N sodium hydroxide (0.81 mL, 0.81 mmol) was added. The solution was stirred at RT overnight, then was concentrated. The residue was dissolved in water/acetonitrile (3 mL), cooled to 0° C., and acidified with TFA (0.21 mL, 2.7 mmol). The solution was concentrated and the residue was purified by reversed-phase flash chromatography to yield the title compound. Anal. [C$_{29}$H$_{30}$N$_4$O$_4$.0.6 (C$_2$HF$_3$O$_2$).1.5(H$_2$O)] calcd: C, 60.55; H, 5.64; N, 9.31. found: C, 60.45; H, 5.80; N, 9.28.

Example 5

Preparation of (R,S)-7-[(4,4'-bipiperidin-1-yl)carbonyl]-4-[2-(cyclohexyl)ethyl]-2,3,4,5-tetrahydro-3-oxo-1H-1,4-benzodiazepine-2-acetic acid a) methyl (R,S)-7-carboxy-4-[2-(cyclohexyl)ethyl]-2,3,4,5-tetrahydro-3-oxo-1H-1,4-benzodiazepine-2-acetate A solution of methyl (R,S)-7-carboxy-2,3,4,5-tetrahydro-3-oxo-4-(2-phenylethyl)-1H-1,4-benzodiazepine-2-acetate (1.2 mmol) and 0.6N hydrochloric acid (4.0 mL) in methanol (50 mL) was treated with platinum oxide (120 mg) and hydrogenated (45 psi) and the mixture was filtered and concentrated to give the title compound.

b) methyl (R,S)-7-[(4,4'-bipiperidin-1-yl)carbonyl]-[2-(cyclohexyl)ethyl]-2,3,4,5-tetrahydro-3-oxo-4-H-1,4-benzodiazepine-2-acetate The compound of Example 5(a) (2.0 mmol) dissolved in DMF (30 mL) was treated with EDC (2.2 mmol) and 1-HOBT (285 mg, 2.1 mmol). This mixture was treated with N-(t-butoxycarbonyl)-4,4'-bipiperidine (2.4 mmol), stirred at RT for 48 h, concentrated and the residue was purified by flash chromatography to yield the title compound.

c) methyl (R,S)-7-[(4,4'-bipiperidin-1-yl)carbonyl]-4-[2-(cyclohexyl)ethyl]-2,3,4,5-tetrahydro-3-oxo-1H-1,4-benzodiazepine-2-acetic acid The compound of Example 5(b) (0.56 mmol) was dissolved in a mixture of CH$_2$Cl$_2$ (25 mL) and TFA (5 mL). After 1 h, the mixture was concentrated to give the title compound.

d) R,S)-7-[(4,4'-bipiperidin-1-yl)carbonyl]-4-[2-(cyclohexyl)ethyl]-2,3,4,5-tetrahydro-3-oxo-1H-1,4-benzodiazepine-2-acetic acid The compound of Example 5(c) (0.3 mmol) was suspended in acetone (2 mL) and treated lithium hydroxide hydrate (25 mg) in water (2 mL). The mixture was stirred overnight, treated with methanol and additional lithium hydroxide hydrate (5.5 mg) was added in two portions over 9 h. The mixture was concentrated and the aqueous residue was neutralized with hydrochloric acid and concentrated. The residue was placed in the refrigerator overnight and filtered. The filter cake was washed with cold water, acetone and ether to yield the title compound Anal. [C$_{30}$H$_{44}$N$_4$O$_4$.2.5 (C$_2$HF$_3$O$_2$) .2(H$_2$O)] calcd: C, 49.70; H, 6.02; N, 6.62. found: C, 49.43; H, 6.02; N, 6.62.

Example 6

Preparation of (R,S)-7-[[4-(2-aminoethyl)piperidin-1-yl]carbonyl]-2,3,4,5-tetrahydro-3-oxo-4-(2-phenylethyl)-1H-1,4-benzodiazepine-2-acetic acid a) methyl (R,S)-7-[[4-(N-t-butoxycarbonyl)(2-aminoethyl)-piperidin-1-yl]carbonyl]-2,3,4,5-tetrahydro-3-oxo-4-(2-phenylethyl)-1H-1,4-benzodiazepine-2-acetate Methyl R,S)-7-carboxy-2,3,4,5-tetrahydro-3-oxo-4-(phenylethyl)-1H-1,4-benzodiazepine-2-acetate (2.0 mmol) dissolved in DMF (30 mL) was treated with DCC (458 mg, 2.2 mmol), 1-HOBT (285 mg, 2.1 mmol) and adjusted to pH 7 with triethylamine. The mixture was treated with N-(t-butoxycarbonyl)-2-(4-piperidinyl)ethanamine (2.4 mmol), stirred at RT for 48 h, concentrated and the residue was purified by flash chromatography to yield the title compound.

b) (R,S)-7-[[4-(2-aminoethyl)piperidin-1-yl]carbonyl]-2,3,4,5-tetrahydro-3-oxo-4-(2-phenylethyl)-1H-1,4-benzodiazepine-2-acetic acid The compound of Example 6(a) (0.56 mmol) was dissolved in a mixture of CH$_2$Cl$_2$ (25 mL) and TFA (5 mL). After 1 h, the mixture was concentrated to give the methyl ester of the title compound.

The methyl ester (0.27 mmol) was dissolved in methanol (9 mL), and 1.0 N sodium hydroxide (0.81 mL, 0.81 mmol) was added. The solution was stirred at RT overnight, then was concentrated. The residue was dissolved in water/acetonitrile (3 mL), cooled to 0° C., and acidified with TFA (0.21 mL, 2.7 mmol). The solution was concentrated and the residue was purified by reversed-phase flash chromatography to yield the title compound. MS(ES) m/e 479 [M+H]$^+$, 477 [M+H]$^-$.

Example 7

Preparation of (R,S)-7-[[(1,2,3,4-tetrahydro-7-isoquinolinyl]amino]carbonyl]-2,3,4,5-tetrahydro-3-oxo-4-(2-phenylethyl)-1H-1,4-benzodiazepine-2-acetic acid Using the procedure of Example 4, except substituting methyl (R,S)-7-carboxy-2,3,4,5-tetrahydro-3-oxo-4-(2-phenylethyl)-1H-1,4-benzodiazepine-2-acetate for methyl (R,S)-8-carboxy-2,3,4,5-tetrahydro-3-oxo-4-(2- phenylethyl)-1H-1,4-benzodiazepine-2-acetate, gave the title compound. Anal. [$C_{29}H_{30}N_4O_4$.2($C_2HF_3O_2$).0.75 ($H_2O$)] calcd: C, 53.55; H, 4.36; N, 7.57. found: C, 53.80; H, 4.56; N, 7.56.

Example 8

Preparation of (R,S)-7-[(4,4'-bipiperidin-1-yl)carbonyl]-2,3,4,5-tetrahydro-4-methyl-3-oxo-1H-1,4-benzodiazepine-2-acetic acid a) t-butyl 3-methyl-4-nitrobenzoate 3-Methyl-4-nitrobenzoic acid (500 g, 2.76 mol) was added to pyridine (1.25 L) and stirred until it dissolved. Benzenesulfonyl chloride (609 g, 3.45 mol) was added rapidly while maintaining the internal temperature <30° C. with an ice bath. A precipitate formed towards the end of the addition and pyridine (500 mL) was added to improve stirring. The mixture was stirred for 30 min and t-butanol (523 mL) was added dropwise over 30 min at <30° C. The mixture was stirred for 2 h, dissolved in hexane:ethyl acetate (4:1; 2.5 L) and the resulting mixture was extracted with water. The organic phase was concentrated to give a light yellow oil which crystallized on cooling to give the title compound (635 g, 97%). mp 56–58° C.

b) t-butyl 3-bromomethyl-4-nitrobenzoate

A solution of the compound of Example 8(a) (635 g, 2.68 mol) in carbon tetrachloride (6 L) was stirred and treated with N-bromosuccinimide (476.5 g, 2.68 mol). The mixture was irradiated and heated to reflux with 3 flood lamps positioned below the solution level. Benzoyl peroxide (6 g) was added in four portions while the mixture was heated to reflux and the last portion was added as reflux was reached after 2 h. The mixture was irradiated at reflux for 12 h, cooled, allowed to stand several hours, filtered and concentrated to a brown oil (870.7 g). The oil was taken up in hexane (3 L) and ether (500 mL) (boiling), filtered and the filtrate was partly concentrated by boiling. The resulting solution was allowed to stand overnight and the off-white crystalline solid which formed was filtered, washed with hexane and dried to give the title compound (396.6 g, 46.8%). mp 80–83° C.; $^1$H NMR (250 MHz) δ 4.5 (2H); TLC $R_f$ 0.7 (silica gel, 1:9 ethyl acetate/hexane). The filtrate yielded a second crop on standing (73 g). mp 61–65° C.

c) t-butyl 3-(methylamino)methyl-4-nitrobenzoate

Aqueous 40% methylamine (623 mL) was added to dimethylformamide (2.5 l) stirred at –5° C. in an acetone/ice bath. A solution of the compound of Example 8(b) (238 g, 0.753 mol) in ethyl acetate (600 mL) was added dropwise over 1 h while maintaining the internal temperature between 0° C. and –5° C. The clear yellow reaction mixture was stirred for an additional 30 min and was diluted with an equal volume of water. Hexane was added, the organic phase was separated and the aqueous phase was extracted with hexane. The combined organic extracts were washed with water and concentrated to give the title compound (217.8 g) as a bright yellow oil.

d) t-butyl 3-[N-(t-butoxycarbonyl)-(methylamino)-methyl]-4-nitrobenzoate

A solution of the compound of Example 8(c) (0.753 mol) in ethyl acetate (1 L) was stirred and treated with di-t-butyl dicarbonate (180.8 g, 0.828 mol) which was added in portions. A vigorous reaction occurred with rapid gas evolution which ceased after the final addition of the dicarbonate. The reaction mixture was stirred for an additional 30 min, and was extracted with 4% aqueous sodium carbonate and with water. The organic phase was concentrated to give a light yellow oil which was dissoved in hexane and cooled in a Dry Ice/acetone bath to initiate crystallization. The mixture was stored in the refrigerator, filtered and dried to give the title compound (129 g, 47%) which was used in the next step. mp 56–58° C. $^1$H NMR (CDCl$_3$) δ 8.05 (2H, s), 7.95 (1H, s), 4.8 (2H, d), 2.9 (2H, s), 1.6 (9H, s), 1.5 (9H, s); HPLC $t_R$ 27 min (Zorbax RX $C_{18}$, gradient, 4.6×150 mm, A:methanol B:water-0.1% TFA, 50–90% methanol during 40 min, UV detection at 210 nm).

e) t-butyl 4-amino-3-[N-(t-butoxycarbonyl)-(methylamino)methyl]benzoate

A solution of the compound of Example 8(d) (129 g, 0.352 mol) in ethyl acetate/methanol (1:1, 1.5 L) was treated with 10% Pd/C (40 g) moistened with ethyl acetate under argon in a hydrogenation bottle. The bottle was purged with hydrogen and shaken until the theoretical amount of hydrogen was absorbed. The mixture filtered through Celite® and the filtrate containing the title compound was used in the next step.

f) t-butyl (E/Z)-3-[N-(t-butoxycarbonyl)(methylamino)methyl]-4-[2-(1,4-dimethoxy-1,4-dioxo-2-butenyl)amino]benzoate A solution of the compound of Example 8(e) (118.3 g, 0.352 mol) in methanol:ethyl acetate (1.5 L) was stirred at RT under argon and dimethyl acetylenedicarboxylate (50 g, 0.352 mol) was added dropwise over 30 min and the mixture was heated to reflux for 16 h. The mixture was cooled and dimethyl acetylenedicarboxylate (6.0 mL, 0.0488 mol) was added in one portion. The reaction mixture was heated to reflux 2.5 h. The resulting solution containing the title compound was cooled and used in the next step.

g) t-butyl (R,S)-3-[N-(t-butoxycarbonyl)-(methylamino)-methyl]-4-[2-(1,4-dimethoxy-1,4-dioxobutyl)amino]benzoate A solution of the compound of Example 8(f) (~168 g, 0.352 mol) in ethyl acetate:methanol (1.5 L) was added to 10% Pd/C (20 g) moistened with ethyl acetate under argon in a hydrogenation bottle. The mixture was shaken in a hydrogen atmosphere and heated to 48° C. until the theoretical amount of hydrogen was absorbed, cooled, vented, filtered through Celite® and the filtrate was concentrated to give the title compound (173.4 g) as a yellow oil. HPLC $t_R$ 18.9 min (Zorbax RX $C_{18}$, 4.6×150 mm, 1 mL/min, gradient, A:methanol B:water-0.1% TFA, 50–90% methanol over 40 min, UV detection at 210 nm).

h) (R,S)-4-[2-(1,4-dimethoxy-1,4-dioxobutyl)amino]-3-[(methylamino)methyl]benzoate A solution of the compound of Example 8(g) (0.348 mol) in dichloromethane (500 mL) was added over 30 min to a stirred solution of TFA (684 mL) and dichloromethane (1550 mL); the internal was between 18° C.–25° C. The solution was stirred overnight at RT and concentrated to give the title compound (254.6 g) as a brown oil. HPLC $t_R$ 19 min (Zorbax RX $C_{18}$ column, 4.6×150 mm, gradient, 1 mL/min, A:methanol B:water-0.1% TFA, 10–60% methanol over 50 min, UV detection at 210 nm).

i) methyl (R,S)-7-carboxy-2,3,4,5-tetrahydro-4-methyl-3-oxo-1H-1,4-benzodiazepine-2-acetate A solution of the compound of Example 8(h) [112.7 g (0.348 mol) with TFA (141.9 g)] in methanol (2 L) was cooled to between 0° C. to –5° C. and stirred under argon. Sodium methoxide in methanol (25%; 396 mL, 1.94 mol) was added over 2 h, maintaining the internal temperature between 0° C. to –5° C. Following the addition, the temperature was allowed to rise slowly and the mixture stirred for 45 min. Glacial acetic acid (42 mL) was added to the reaction mixture followed by water (1.5 L). A crystalline precipitate began to form and the pH of the mixture was adjusted to 4.5 by careful additions of 12N hydrochloric acid. The mixture was stirred a few min, filtered and the precipitate washed with water and vacuum dried to give the title compound (77.6 g, 76%). $^1$H NMR (250 MHz, DMSO$_{d6}$) δ 7.5 (2H, m), 6.5 (2H, m), 5.5 (1H, d), 5.2 (1H, m), 3.9 (1H, d), 3.6 (3H, s), 2.9 (3H, s), 2.9–2.6 (2H, m); mp 276–277° C., HPLC tR 23.2 min (Zorbax RX C18, 4.6×150 mm, 1 mL/min, gradient, A:methanol B:water-0.1% TFA, 10–60% methanol over 50 min, UV detection at 210 nm); Anal. (C$_{14}$H$_{16}$N$_2$O$_5$) calcd: C, 57.53; H, 5.52; N, 9.58. found: C, 57.27; H, 5.41; N, 9.17; mp 280–280.5° C. (dec).

j) methyl (R,S)-7-[[1'-(t-butoxycarbonyl)-4,4'-bipiperidin-1-yl]carbonyl]-2,3,4,5-tetrahydro-4-methyl-3-oxo-1H-1,4-benzodiazepine-2-acetate Using the procedure of Example 5(b), except substituting the compound of Example 8(i) for methyl (R,S)-7-carboxy-2,3,4,5-tetrahydro-3-oxo-4-(2-phenylethyl)-1H-1,4-benzodiazepine-2-acetate, gave the title compound.

k) methyl (R,S)-7-[(4,4'-bipiperidin-1-yl)carbonyl]-2,3,4,5-tetrahydro-4-methyl-3-oxo-1H-1,4-benzodiazepine-2-acetate Using the procedure of Example 5(c), except substituting the compound of Example 8(j) for the compound of Example 5(b), gave the title compound.

l) (R,S)-7-[(4,4'-bipiperidin-1-yl)carbonyl]-2,3,4,5-tetrahydro-4-methyl-3-oxo-1H-1,4-benzodiazepine-2-acetic acid Using the procedure of Example 5(d), except substituting the compound of Example 8(k) for the compound of Example 5(c) and substituting sodium hydroxide for lithium hydroxide, gave the title compound. Anal. [C$_{23}$H$_{32}$N$_4$O$_4$.2(C$_2$HF$_3$O$_2$)].2.5(H$_2$O)] calcd: C, 46.22; H, 5.46; N, 7.99. found: C, 46.33, H, 5.45; N, 7.97.

Example 9

Preparation of (R,S)-2,3,4,5-tetrahydro-3-oxo-2-(2-phenylethyl)-7-[[[2-(1-piperazinyl)ethyl] methylamino]-carbonyl]-1H-2-benzazepine-4-acetic acid a) methyl (R,S)-7-[[[2-[4-(benzyloxycarbonyl)-1-piperazinyl)]ethyl]methylamino]carbonyl]-2,3,4,5-tetrahydro-3-oxo-2-(2-phenylethyl)-1H-2-benzazepine-4-acetate Methyl (R,S)-7-carboxy-2,3,4,5-tetrahydro-3-oxo-2-(2-phenylethyl)-1H-2-benzazepine-4-acetate (2.0 mmol) dissolved in DMF (30 mL) was treated with DCC (458 mg, 2.2 mmol), 1-HOBT (285 mg, 2.1 mmol) and adjusted to pH 7 with triethylamine. The mixture was treated with 2-[1-[4-(benzyloxycarbonyl)piperazinyl]]-N-methylethanamine (2.4 mmol), stirred at RT for 48 h, concentrated and the residue was purified by flash chromatography to yield the title compound.

b) (R,S)-2,3,4,5-tetrahydro-3-oxo-2-(2-phenylethyl)-7-[[[2-(1-piperazinyl)ethyl]methylamino]carbonyl]-1H-2-benzazepine-4-acetic acid The compound of Example 9(a) (0.3 mmol) was dissolved in methanol (20 mL), and added to palladium hydroxide (100 mg) and 3N hydrochloric acid (1 mL). The mixture was hydrogenated (40 psi) for 6 h. The reaction mixture was filtered, the catalyst washed with acetonitrile and the filtrate concentrated.

The methyl ester (200 mg, 0.3 mmol) was dissolved in methanol (4 mL) and 1N sodium hydroxide (0.5 mL), stirred, concentrated, diluted with water, acidified with 3N hydrochloric acid and concentrated. The residue was chromatographed by HPLC to yield the title compound as white solid.

Example 10

Preparation of (R,S)-2-butyl-2,3,4,5-tetrahydro-3-oxo-7-[[[2-(piperidin-4-yl)ethyl]methylamino] carbonyl]-1H-2-benzazepine-4-acetic acid 1-(3-Dimethylaminopropyl)-3-ethylcarbodiimide hydrochloride (1.19 g, 6.23 mmol) was added all at once to a solution of methyl (R,S)-7-carboxy-2,3,4,5-tetrahydro-3-oxo-1H-2-benzazepine-4-acetate (1.44 g, 5.19 mmol), benzyl alcohol (2.7 mL, 25.95 mmol), diisopropylethylamine (1.8 mL, 10.38 mmol), and 4-(dimethylamino)pyridine (761 mg, 6.23 mmol) in anhydrous dimethylformamide (26 mL) at RT. The reaction was stirred for 24 h and concentrated to leave a pale yellow oil. The oil was diluted with ethyl acetate (200 mL), and the cloudy mixture was washed sequentially with 1N hydrochloric acid and water. The combined aqueous layers were extracted with ethyl acetate, and the combined organic layers were dried (MgSO$_4$) and concentrated. Chromatography over silica gel gave methyl (R,S)-7-benzyloxycarbonyl-2,3,4,5-tetrahydro-3-oxo-1H-2-benzazepine-4-acetate (1.59 g, 83%).

methyl (R,S)-7-benzyloxycarbonyl-2,3,4,5-tetrahydro-3-oxo-1H-2-benzazepine-4-acetate (220.4 mg, 0.60 mmol) was suspended in toluene (5–10 mL), and the mixture was carefully concentrated to remove water and residual solvents. The resulting solid was dissolved in dry 1:1 THF:DMF (12 mL), and 1-iodobutane (3.0 mmol) was added. Sodium hydride (60% in mineral oil, 29 mg, 0.72 mmol) was added, causing gas evolution and slight warming. After 15 min, the reaction was cooled to 0° C. and quenched with saturated aqueous ammonium chloride (2 mL). The mixture was diluted with ether (50 mL) and washed with water. The combined aqueous layers were extracted with ether, and the combined organic layers were dried (MgSO$_4$) and concentrated. Chromatography over silica gel yielded methyl (R,S)-7-benzyloxycarbonyl-2,3,4,5-tetrahydro-2-butyl-3-oxo-1H-2-benzazepine-4-acetate.

10% Pd/C (64 mg, 0.06 mmol) was added carefully to a solution of methyl (R,S)-7-benzyloxycarbonyl-2,3,4,5-tetrahydro-2-butyl-3-oxo-1H-2-benzazepine-4-acetate (0.60 mmol) in methanol (12 mL). The mixture was purged with hydrogen and stirred briskly at RT under hydrogen (balloon pressure). After 15 h, the reaction was filtered through Celite®, and the filtrate was concentrated to afford methyl (R,S)-7-carboxy-2,3,4,5-tetrahydro-2-butyl-3-oxo-1H-2-benzazepine-4-acetate.

1-(3-dimethylaminopropyl)-3-ethylcarbodiimide hydrochloride (90 mg, 0.47 mmol) was added to a solution of methyl (R,S)-7-carboxy-2,3,4,5-tetrahydro-2-methyl-3-oxo-1H-2-benzazepine-4-acetate (0.39 mmol), N-methyl-2-(pyrid-4-yl)ethanamine (64 mg, 0.47 mmol), 1-hydroxybenzotriazole (63 mg, 0.47 mmol), and diisopropylethylamine (0.14 mL, 0.78 mmol) in dry dimethylformamide (2 mL) at RT under argon. The reaction was stirred for 23 h and concentrated. The residue was partitioned between ethyl acetate and water. The layers were separated, and the organic phase was washed with water. The combined aqueous layers were back-extracted with ethyl acetate, the combined organic layers were dried (sodium sulfate) and concentrated to leave a yellow oil. The combined aqueous layers were concentrated and sodium chloride was added. The resulting mixture was exhaustively extracted with chloroform. The combined organic phase was dried (sodium sulfate) and concentrated to give a yellow oil, which was combined with the material from the ethyl acetate phase. Chromatography over silica gel yielded methyl (R,S)-2,3,4,5-tetahydro-2-butyl-3-oxo-7-[[[2-(pyrid-4-yl)ethyl] methylamino]carbonyl]-1H-2-benzazepine-4-acetate.

Platinum oxide (4 mg) was added to a solution of methyl (R,S)-2,3,4,5-tetrahydro-2-butyl-3-oxo-7-[[[2-(pyrid-4-yl) ethyl]methylamino]carbonyl]-1H-2-benzazepine-4-acetate (0.35 mmol) and 1N hydrochloric acid (0.35 mL, 0.35 mmol) in methanol (3.5 mL), and the mixture was stirred briskly under H$_2$ (balloon pressure). After 7 h, the reaction was filtered through Celite® and concentrated, and the residue was dissolved in methanol (3.5 mL). Platinum oxide (4 mg) was added, and the mixture was stirred briskly under $H_2$ (balloon pressure) for 16.5 h. Filtration through Celite® and concentration yielded methyl (R,S)-2,3,4,5-tetrahydro-2-butyl-3-oxo-7-[[[2-(piperidin-4-yl)ethyl]methylamino] carbonyl]-1H-2-benzazepine-4-acetate.

Methyl (R,S)-2,3,4,5-tetrahydro-2-butyl-3-oxo-7-[[[2-(piperidin-4-yl)ethyl]methylamino]carbonyl]-1H-2-benzazepine-4-acetate was dissolved in methanol (12 mL) and cooled to 0° C. 1N Sodium hydroxide (1.05 mL, 1.05 mmol) was added dropwise, and the solution was allowed to warm to RT. The reaction was stirred at RT for 24 h and concentrated. The residue was concentrated from 1:1 acetonitrile:water (4 mL) to remove methanol, the residue dissolved in 1:1 acetontrile:water (4 mL), and cooled in ice. TFA (0.27 mL, 3.5 mmol) was added and the reaction was concentrated. The residue was purified by reversed-phase flash chromatography. Concentration and lyophilization gave the title compound. MS(ES) m/e 444 $[M+H]^+$.

Examples 11–12 a) Using the procedure of Example 10 to alkylate the 2-amino group and debenzylate the benzyl ester, except substituting benzyl bromide or (5-iodopentyl)benzene for iodobutane, and using the procedure of Example 1(a)–(b), except substituting Pd/C for palladium hydroxide, yielded the following compounds: 11(a). methyl 2-benzyl-2,3,4,5-tetrahydro-3-oxo-7-[[[2-(piperidin-4-yl)ethyl]methylamino] carbonyl]-1H-2-benzazepine-4-acetate. MS(ES) m/e 492 $[M+H]^+$. 12(a). methyl 2,3,4,5-tetrahydro-3-oxo-2-(5-phenylpentyl)-7-[[[2-(piperidin-4-yl)ethyl]methylamino] carbonyl]-1H-2-benzazepine-4-acetate. MS(ES) m/e 548 $[M+H]^+$.

b) Using the procedure of Example 1(c), except substituting the compounds of Example 11–12(a) for the compound of Example 1(b), gave the following compounds: 11(b). 2-benzyl-2,3,4,5-tetrahydro-3-oxo-7-[[[2-(piperidin-4-yl) ethyl]methylamino]carbonyl]-1H-2-benzazepine-4-acetate. 12(b). 2,3,4,5-tetrahydro-3-oxo-2-(5-phenylpentyl)-7-[[[2-(piperidin-4-yl)ethyl]methylamino]carbonyl]-1H-2-benzazepine-4-acetate.

Example 13

Preparation of (R,S)-7-[[[4-(aminoiminomethyl) phenyl]methyl-amino]carbonyl]-2,3,4,5-tetrahydro-2-isopropyl-3-oxo-1H-2-benzazepine-4-acetic acid Using the procedure of Preparation 8(c)–(j), except substituting isopropylamine for 2-phenethylamine in the procedure of Preparation 8(c) and substituting 2,4,6-collidine for sodium methoxide in methanol in the procedure of Preparation 8(g), gave the title compound. MS(ES) m/e 437 $[M+H]^+$.

Examples 14–17

Using the procedures of Preparation 8(c)–(g), except substituting a) isopropylamine, b) isopentylamine, c) 3,3-dimethylbutylamine or d) cyclohexylamine for phenethylamine in the procedure of Preparation 8(c), and optionally substituting 2,4,6-collidine, triethylamine in toluene, or diisopropylethylamine in xylene, for sodium methoxide in methanol in the procedure of Preparation 8(g), and subsequently using the procedure of Example 2(b)–(d), except optionally substituting benzotriazol-1-yloxy-tris (dimethylamino)-phosphonium hexafluorophosphate for 1-(3-dimethylamino-propyl)-3-ethylcarbodiimide, gave the following compounds: 14. (R,S)-2,3,4,5-tetrahydro-2-isopropyl-3-oxo-7-[[[2-(4-piperidinyl)ethyl]methylamino] carbonyl]-1H-2-benzazepine-4-acetic acid. MS(ES) m/e 430 $[M+H]^+$. 15. (R,S)-2,3,4,5-tetrahydro-2-isopentyl-3-oxo-7-[[[2-(4-piperidinyl)ethyl]methylamino]carbonyl]-1H-2-benzazepine acetic acid. MS(ES) m/e 458 $[M+H]^+$. 16. (R,S)-2-(3,3-dimethylbutyl)-2,3,4,5-tetrahydro-3-oxo-7-[[[2-(4-piperidinyl)ethyl]methylamino]carbonyl]-1H-2-benzazepine-4-acetic acid. MS(ES) m/e 472 $[M+H]^+$. 17. (R,S)-2-cyclohexyl-2,3,4,5-tetrahydro-3-oxo-7-[[[2-(4-piperidinyl)ethyl]methylamino]carbonyl]1-H-2-benzazepine-4-acetic acid. MS(ES) m/e 470 $[M+H]^+$.

Example 18

Preparation of (R,S)-2-[2-(4-fluorophenyl)ethyl]-2, 3,4,5-tetrahydro-3-oxo-7-[[[2-(4-piperidinyl)ethyl] methylamino]-carbonyl]-1H-2-benzazepine-4-acetic acid Using the procedure of Preparation 8(c)–(g), except substituting 4-(fluoro)phenethylamine for phenethylamine in the procedure of Preparation 8(c) and substituting diisopropylethylamine in xylene for sodium methoxide in methanol in the procedure of Preparation 8(g), and using the procedure of Example 1, gave the title compound. MS(ES) m/e 510 $[M+H]^+$.

Example 19

Preparation of (R,S)-7-[[[4-(aminoiminomethyl) phenyl]-carbonyl]amino]-2,3,4,5-tetrahydro-3-oxo-2-(2-phenylethyl]1-H-2-benzazepine-4-acetic acid a) methyl (R,S)-7-amino-2,3,4,5-tetrahydro-3-oxo-2-(2-phenylethyl]-1H-2-benzazepine-4-acetate A mixture of methyl (R,S)-7-carboxy-2,3,4,5-tetrahydro-3-oxo-2-(2-phenylethyl)-1H-2-benzazepine-4-acetate (2.67 mmol), triethylamine (0.42 mL, 5.87 mmol) and diphenyl phosphorylazide (0.62 mL, 2.80 mmol) in toluene (20 mL) was heated at 105° C. for 0.5 h. After the temperature was lowered to 80° C., the mixture was treated with benzyl alcohol (0.60 mL, 0.42 mmol), stirred for 14 h and concentrated. The residue was purified by flash chromatography to give methyl (R,S)-7-(carbobenzyloxy)amino-2,3,4,5-tetrahydro-3-oxo-2-(2-phenylethyl)-1H-2-benzazepine-4-acetate.

The Cbz compound (0.68 g, 1.38 mmol) was dissolved in methanol (10 mL) and palladium on carbon (5%, 50 mg) was added. The mixture was hydrogenated for 1 h, filtered through Celite® and concentrated to yield the title compound.

b) methyl (R,S)-7-[[[4-(N-benzyloxycarbonyl)-(aminoimiomethyl)phenyl]carbonyl]amino]-2,3,4,5-tetrahydro-3-oxo-2-(2-phenylethyl)-1H-2-benzazepine-4-acetate 4-[N-(benzyloxycarbonyl)(aminoiminomethyl)]benzoic acid (2.0 mmol) dissolved in DMF (30 mL) was treated with 1-(3-dimethylaminopropyl)-3-ethylcarbodiimide hydrochloride (2.2 mmol), 1-HOBT (285 mg, 2.1 mmol) and adjusted to pH 7 with diisopropylethylamine. The mixture was treated with the compound of Example 19(a) (2.4 mmol), stirred at RT for 48 h, concentrated and the residue was purified by flash chromatography to yield the title compound.

c) methyl (R,S)-7-[[[4-(aminoimiomethyl)phenyl] carbonyl]-amino]-2,3,4,5-tetrahydro-3-oxo-2-(2-phenylethyl]-1H-2-benzazepine-4-acetate A solution of the compound of Example 19(b) (0.15 mmol) and 10% Pd/C (20 mg) in methanol (40 mL) and acetic acid (8 drops) was shaken in a hydrogen atmosphere (45 psi) for 30 min. The mixture was filtered and the filtrate concentrated in vacuo to yield the title compound.

d) methyl (R,S)-7-[[[4-(aminoiminomethyl)phenyl] carbonyl]-amino]-2,3,4,5-tetrahydro-3-oxo-2-(2-phenylethyl]-1H-2-benzazepine-4-acetate A solution of the compound of Example 19(c) (65 mg, 0.12 mmol) was stirred in lithium hydroxide in aqueous THF at room temperature under argon overnight. The mixture was treated with 3N HCl (1 mL) and concentrated in vacuo. The residue was purified by HPLC. MS(ES) m/e 485 [M+H]$^+$, 483 {M-H]$^-$.

Example 20

Preparation of (R,S)-2-[2-(cyclohexyl)ethyl]-2,3,4, 5-tetrahydro-3-oxo-7-[[[2-(4-piperidinyl)ethyl] carbonyl]amino]-1H-2-benzazepine-4-acetic acid a) methyl (R,S)-2,3,4,5-tetrahydro-3-oxo-7-[[[2-(4-pyridyl) ethyl]carbonyl]amino]-2-(phenylethyl)-1H-2-benzazepine-4-acetate Using the procedure of Example 19(b), except substituting 4-(pyridyl)propionic acid for 4-[N-(benzyloxycarbonyl) (aminoiminomethyl)]benzoic acid, gave the title compound.

b) (R,S)-2-[2-(cyclohexyl)ethyl]-2,3,4,5-tetrahydro-3-oxo-7-[[[2-(4-piperidinyl)ethyl]carbonyl]amino]-1H-2-benzazepine-4-acetate Using the procedure of Example 2(c), except substituting the compound of Example 20(a) for the compound of Example 2(b) and subsequently using the procedure of Example 2(d) except substituting lithium hydroxide in aqueous THF for sodium hydroxide in aqueous methanol, gave the title compound. MS(ES) m/e 484 [M+H]$^+$, 482 [M-H]$^-$.

Example 21

Preparation of (R,S)-8-[(4,4'-bipiperidin-1-yl) carbonyl]-2,3,4,5-tetrahydro-3-oxo-2-(2-phenylethyl)-1H-2-benzazepine-4-acetic acid a) methyl (R,S)-8-carboxy-2,3,4,5-tetrahydro-3-oxo-2-(2-phenylethyl)-1H-1,4-benzodiazepine-4-acetate Using the procedure of Preparation 8(a)–(g), except substituting 4-bromo-3-methylbenzoic acid for 3-bromo-4-methylbenzoic acid, gave the title compound.

b) (R,S)-8-[(4,4'-bipiperidin-1-yl)carbonyl]-2,3,4,5-tetrahydro-3-oxo-4-(2-phenylethyl)-1H-2-benzodiazepine-4-acetic acid Using the procedure of Example 5(b)–(d), except substituting the compound of Example 21(a) for the compound of Example 5(a) gave the title compound. Anal. ($C_{31}H_{39}N_3O_4 \cdot H_2O$) calcd: C, 69.78; H, 7.71; N, 7.84. found: C, 69.38; H, 7.68; N, 7.37.

Example 22

Preparation of (R,S)-2,3,4,5-tetrahydro-3-oxo-2-(2-phenylethyl)-7-[[[2-(4-piperidinyl)ethyl]-methylamino]carbonyl]-1H-2-benzazepine-4-propionic acid a) ethyl 5-[5-(t-butoxycarbonyl)-2-[[[N-(t-butoxycarbonyl)-N-(2-phenylethyl)]amino]methyl]phenyl]-4-ethoxycarbonyl-4-pentenoate; and ethyl 5-[5-(t-butoxycarbonyl)-2-[[[N-(t-butoxycarbonyl)-N-(2-phenylethyl))]amino]methyl]phenyl]-4-ethoxycarbonyl-3-pentenoate.

Using the procedure of Preparation 8(e), except substituting diethyl 2-methyleneglutarate [*Tet. Lett.,* 30, 7381 (1989)] for dimethyl itaconate, gave the title compounds.

b) ethyl 5-[5-(t-butoxycarbonyl)-2-[[[N-(t-butoxycarbonyl)-N-(2-phenylethyl)]amino]methyl]phenyl]-4-(ethoxycarbonyl)-pentanoate Using the procedure of Preparation 8(f), except substituting the compound of Example 22(a) for the compound of Preparation 8(e) and substituting Pd/C in ethanol:ethyl acetate for palladium hydroxide in methanol, gave the title compound.

c) ethyl (R,S)-7-carboxy-2,3,4,5-tetrahydro-3-oxo-2-(2-phenylethyl)-1H-2-benzazepine-4-propanoate Using the procedure of Preparation 8(g), except substituting the compound of Example 22(b) for the compound of Preparation 8(f) and substituting hydrogen chloride in dioxane for TFA, gave the title compound.

d) (R,S)-2,3,4,5-tetrahydro-3-oxo-2-(2-phenylethyl)-7-[[[2-(4-piperidinyl)ethyl]methylamino]carbonyl]-1H-2-benzazepine-4-propionic acid Using the procedure of Example 1, except substituting the compound of Example 22(c) for methyl (R,S)-8-carboxy-2, 3,4,5-tetrahydro-4-methyl-3-oxo-1H-1,4-benzodiazepine-2-acetate, gave the title compound. MS(ES) m/e 506 [M+H]$^+$, 540 [M-H]$^-$; Anal. ($C_{30}H_{39}N_3O_4 \cdot HCl \cdot 3/8H_2O$) calcd: C, 65.68; H, 7.48; N, 7.66. found: C, 65.67; H, 7.55.

Example 23–24 a) Methyl (R,S)-7-[1'-(t-butoxycarbonyl)-4,4'-bipiperidin-1-yl]carbonyl]-2,3,4,5-tetrahydro-3-oxo-4-(phenylethyl)-1H-1,4-benzodiazepine-2-acetate was chromatographed HPLC t$_R$ 16 min and 19.8 min (Chiracel® OD, 21.1×250 mm, 10 mL/min, methanol, UV detection at 250 nm) to give the following compounds: 23(a). methyl (+)-7-[1'-(t-butoxycarbonyl)-4,4'-bipiperidin-1-yl]carbonyl]-2,3,4,5-tetrahydro-3-oxo-4-(phenylethyl)-1H-1,4-benzodiazepine-2-acetate. 24(a). methyl (−)-7-[1'-(t-butoxycarbonyl)-4,4'-bipiperidin-1-yl]carbonyl]-2,3,4,5-tetrahydro-3-oxo-4-(phenylethyl)-1H-1,4-benzodiazepine-2-acetate.

b) Using the procedure of Example 5(c)–(d), except substituting the compounds of Example 23–24(a) for the compound of Example 5(b), gave the following compounds: 23(b). (+)-7-[(4,4'-bipiperidin-1-yl)carbonyl]-2,3,4,5-tetrahydro-3-oxo-4-(phenylethyl)-1H-1,4-benzodiazepine-2-acetic acid; [α]$_D$ +128 (c 0.5,$CH_{30}$H); [α]D +80 (c=0.5 water); Anal. ($C_{30}H_{38}N_4O_4 \cdot 2C_2HF_3O_2 \cdot 1.5H_2O$) calcd: C, 52.78, H, 5.60, N, 7.24. found: C, 52.70, H, 5.89, N, 7.47. 24(b). (−)-7-[(4,4'-bipiperidin-1-yl)carbonyl]-2,3,4,5-tetrahydro-3-oxo-4-(phenylethyl)-1H-1,4-benzodiazepine-2-acetic acid: [α]$_D$ −118 (c 0.5,$CH_3OH$); Anal. ($C_{30}H_{38}N_4O_4 \cdot 2C_2HF_3O_2$) calcd: C, 54.69, H, 5.40, N, 7.50. found: C, 54.49, H, 5.40, N, 7.85.

Example 25

Preparation of (R,S)-7-[[(4,4'-bipiperidin-1-yl)] carbonyl]-2,3,4,5-tetrahydro-4-isopropyl-3-oxo-1H-1,4-benzodiazepine-2-acetic acid a) methyl (R,S)-7-carboxy-4-isopropyl-2,3,4,5-tetrahydro-3-oxo-1H-1,4-benzodiazepine-2-acetate Using the procedure of Preparation 7(b)–(f), except substituting isopropylamine for phenethylamine in Preparation 7(b) and substituting diisopropylethylamine in refluxing xylene for sodium methoxide in methanol in Preparation 7(f), gave the title compound.

b) methyl (R,S)-7-[[(4,4'-bipiperidin-1-yl)]carbonyl]-2,3,4, 5-tetrahydro-4-isopropyl-3-oxo-1H-1,4-benzodiazepine-2-acetate Using the procedure of Example 5(b)–(c), except substituting the compound of Example 25(a) for the compound of Example 5(a) gave the title compound.

c) (R,S)-7-[[(4,4'-bipiperidin-1-yl)]carbonyl]-2,3,4,5-tetrahydro-4-isopropyl-3-oxo-1H-1,4-benzodiazepine-2-acetic acid Using the procedure of Preparation 8(j), except substituting the compound of Example 25(b) for the compound of Preparation 8(i), gave the title compound. HPLC k' 4.27 (PRP-1; 15% acetonitrile/water/0.1% TFA); $^1$H NMR (400 MHz, CD$_3$OD) δ 7.12 (d, J=1.9 Hz, 1H), 7.08 (dd, J=8.3, 1.9 Hz, 1H), 6.59 (d, J=8.3 Hz, 1H), 5.29 (d, J=17.0 Hz, 1H), 5.17 (dd, J=8.9, 5.2 Hz, 1H), 4.72–4.84 (m, 1H), 4.10 (d, J=17.0 Hz, 1H), 3.34–3.45 (m, 2H), 2.70–3.15 (m, 5H), 2.63 (dd, J=16.8, 5.2 Hz, 1H), 1.92–2.05 (m, 2H), 1.69–1.88 (m, 2H), 1.35–1.54 (m, 4H), 1.16–1.31 (m, 2H), 1.20 (d, J=6.8 Hz, 3H), 1.03 (d, J=6.9 Hz, 3H); MS(ES) m/e 457.2 [M+H]$^+$; Anal. (C$_{25}$H$_{36}$N$_4$O$_4$·1.5 CF$_3$CO$_2$H·1.5 H$_2$O) calcd: C, 51.37; H, 6.24; N, 8.56. found: C, 51.49; H, 6.39; N, 8.46.

Examples 26–27

Preparation of (R)-7-[(4,4'-bipiperidin-1-yl)carbonyl]-2,3,4,5-tetrahydro-4-methyl-3-oxo-1H-1,4-benzodiazepine-2-acetic acid; and (S)-7-[(4,4'-bipiperidin-1-yl)carbonyl]-2,3,4,5-tetrahydro-4-methyl-3-oxo-1H-1,4-benzodiazepine-2-acetic acid a) The compound of Example 8(j) was separated by chiral HPLC to give the following compounds: 26(a). methyl (R)-7-[[1'-(t-butoxycarbonyl)-4,4'-bipiperidin-1-yl]carbonyl]-2,3,4,5-tetrahydro-4-methyl-3-oxo-1H-1,4-benzodiazepine-2-acetate. [α]$_D$ +140 (c 1,CH$_3$OH); HPLC t$_R$ 12.9 min (Chiralcel OD, 21.2×250 mm, 10 mL/min, methanol, UV detection at 325 nm) 27(b). methyl (S)-7-[[1'-(t-butoxycarbonyl)-4,4'-bipiperidin-1-yl]carbonyl]-2,3,4,5-tetrahydro-4-methyl-3-oxo-1H-1,4-benzodiazepine-2-acetate. [α]$_D$ −142.5 (c 1,CH$_3$OH); HPLC t$_R$ 15.1 min (Chiralcel OD, 21.2×250 mm, 10 mL/min, methanol, UV detection at 325 nm).
b) Using the procedure of Example 8(k), except substituting the compounds of Example 26(a) and 27(a) for the compound of Example 8(j) gave the following compounds: 26(b). methyl (R)-7-[(4,4'-bipiperidin-1-yl)carbonyl]-2,3,4,5-tetrahydro-4-methyl-3-oxo-1H-1,4-benzodiazepine-2-acetate. HPLC t$_R$ 14.3 min (Ultrasphere C18, 4.6×250 mm, 1.5 mL/min, gradient, A:acetonitrile B: water-0.1% TFA, 5–60% acetonitrile over 20 min, UV detection at 220 nm) 27(b). methyl (S)-7-[(4,4'-bipiperidin-1-yl)carbonyl]-2,3,4,5-tetrahydro-4-methyl-3-oxo-1H-1,4-benzodiazepine-2-acetate. HPLC t$_R$ 14.61 min (Ultrasphere C18, 4.6×250 mm, 1.5 mL/min, gradient, A:acetonitrile B: water-0.1% TFA, 5–60% acetonitrile over 20 min, UV detection at 220 nm).
c) Using the procedure of Preparation 8(j), except substituting the compounds of Example 26(b) and 27(b) for the compound of Preparation 8(i) gave the following compounds: 26(c). (R)-7-[(4,4'-bipiperidin-1-yl)carbonyl]-2,3,4,5-tetrahydro-4-methyl-3-oxo-1H-1,4-benzodiazepine-2-acetate: [α]$_D$ +92.4 (c 0.5,CH$_3$OH); MS(ES) m/e 429 [M+H]$^+$; 427 [M−H]$^−$; HPLC t$_R$ 12.7 min (Ultrasphere C18, 4.6×250 mm, 1.5 mL/min, gradient, A:acetonitrile B: water-0.1% TFA, 5–60% acetonitrile over 20 min, UV detection at 220 nm); Anal. (C$_{23}$H$_{32}$N$_4$O$_4$·4.5 CF$_3$CO$_2$H·3.33 H$_2$O) calcd: C, 37.44; H, 4.16; N, 5.29. found: C, 37.43; H, 3.81; N, 5.20. 27(c). (S)-7-[(4,4'-bipiperidin-1-yl)carbonyl]-2,3,4,5-tetrahydro-4-methyl-3-oxo-1H-1,4-benzodiazepine-2-acetate: [α]$_D$ −105.9 (c 0.6,CH$_3$OH); MS(ES) m/e 429 [M+H]$^+$; 427 [M−H]$^−$; HPLC t$_R$ 12.6 min (Ultrasphere C18, 4.6×250 mm, 1.5 mL/min, gradient, A:acetonitrile B: water-0.1% TFA, 5–60% acetonitrile over 20 min, UV detection at 220 nm); Anal. (C$_{23}$H$_{32}$N$_4$O$_4$·3 CF$_3$CO$_2$H·1.25 H$_2$O) calcd: C, 43.92; H, 4.77; N, 7.06. found: C, 44.09; H, 5.00; N, 7.29.

Example 28

Preparation of (S)-7-[(4,4'-bipiperidin-1-yl)carbonyl]-2,3,4,5-tetrahydro-4-methyl-3-oxo-1H-1,4-benzodiazepine-2-acetic acid a) 4-fluoro-3-methylbenzoic acid A solution of 4-fluoro-3-methylphenylmagnesium bromide in THF (1.0 M, 250 mL, 250 mmol) was added in a stream over 5 min to a mixture of Dry Ice (10 g) in dry THF (250 mL), and the reaction was allowed to warm to RT and concentrated. The residue was partitioned between water (500 mL) and ether (250 mL), and the layers were separated. The aqueous layer was washed with ether (2×250 mL) and acidified to pH 1 with concentrated hydrochloric acid. The resulting mixture was cooled in an ice bath and filtered. The solid was washed with water and dried to afford the title compound (25.92 g, 67%) as an off-white solid: $^1$H NMR (400 MHz, CDCl$_3$) δ 7.90–8.02 (m, 2H), 7.09 (t, J=8.9 Hz, 1H), 2.34 (d, J=1.7 Hz, 3H); IR (chloroform) 3400–2300 (broad), 1694 cm$^{-1}$; MS(ES) m/e 155 [M+H$^+$; m/e 153 [M−H]$^−$.
b) t-butyl 4-fluoro-3-methylbenzoate Isobutylene was bubbled into a suspension of the compound of Example 28(a) (3.08 g, 20 mmol) in anhydrous ether (15 mL) in a pressure bottle at −78° C. to give a reaction volume of 50 mL. Trifluoromethanesulfonic acid (0.09 mL, 1 mmol) was added dropwise, and the vessel was tightly sealed and warmed to RT. After 4 h, the reaction was cooled and the vessel was opened. Aqueous 5% sodium bicarbonate was added, and the mixture was stirred in a warm water bath to remove the excess isobutylene. Ether was added and the layers were separated. The ether layer was washed with 5% sodium bicarbonate and with brine, and dried (MgSO$_4$). Concentration gave the title compound (3.83 g, 91%) as a yellow oil which was used without further purification: TLC (toluene) R$_f$ 0.73; $^1$H NMR (250 MHz, CDCl$_3$) δ 7.77–7.89 (m, 2H), 7.01 (t, J=8.9 Hz, 1H), 2.30 (d, J=1.8 Hz, 3H), 1.59 (s, 9H); IR (CCl$_4$) 1715, 1369, 1296, 1258, 1167, 1124, 1117, 1105 cm$^{-1}$; MS(ES) m/e 443 [2M+Na]$^+$, 421 [2M+H]$^+$, 211 [M+H]$^+$, 155 [M+H-C$_4$H$_8$]$^+$.
c) t-butyl 4-fluoro-3-(methylaminomethyl)benzoate A mixture of the compound of Example 28(b) (3.83 g, 18.22 mmol), N-bromosuccinimide (3.57 g, 20.24 mmol), benzoyl peroxide (0.22 g, 0.91 mmol), and carbon tetrachloride (90 mL) was heated at reflux. After 16 h, the reaction was cooled in an ice bath, filtered, and the filtrate was concentrated. The residue was passed through a short pad of silica gel which was then washed with 20% ethyl acetate:hexane, and the filtrate was concentrated. The residue was dissolved in THF (90 mL), and 40% aqueous methylamine (7.9 mL, 91.1 mmol) was added rapidly. The reaction was stirred overnight and concentrated. The residue was diluted with ether and washed sequentially with 1.0 N sodium hydroxide, water, and brine. The organic phase was dried (MgSO$_4$), concentrated, and the residue was chromatographed (silica gel, 10% methanol in 1:1 ethyl acetate:chloroform) to give the title compound (2.58 g, 59%) as a yellow oil: TLC R$_f$ 0.49 (silica gel, 10% methanol in 1:1 ethyl acetate/chloroform); $^1$H NMR (250 MHz, CDCl$_3$) δ 7.97 (dd, J=7.3, 2.3 Hz, 1H), 7.90 (ddd, J=8.4, 5.2, 2.3 Hz, 1H), 7.07 (app t, 1H), 3.83 (s, 2H), 2.46 (s, 3H), 1.59 (s, 9H); IR (CCl$_4$) 1714, 1368, 1297, 1248, 1164, 1106 cm$^{-1}$; MS(ES) m/e 240 [M+H]$^+$, 184 [M+H-C$_4$H$_8$]$^+$.
d) t-butyl (S)-4-fluoro-3-[[[4-methoxy-1,4-dioxo-2-[[benzyloxycarbonyl]amino]butyl]methylamino]methyl]benzoate Dicyclohexylcarbodiimide (453.9 mg, 2.2 mmol) was added to a solution of the compound of Example 28(c) (478.6 mg, 2 mmol), N-Cbz-L-aspartic acid β-methyl ester [*J. Am. Chem. Soc.,* 79, 5697 (1957); *J. Am. Chem. Soc.,* 85, 2483 (1963)] (618.8 mg, 2.2 mmol), and 1-hydroxybenzotriazole hydrate (297.3 mg, 2.2 mmol) in anhydrous dimethylformamide (5 mL) at RT. After 24 h, the mixture was diluted with ether (25 mL) and filtered. The filtrate was concentrated, and the residue was diluted with ether (50 mL) and washed with water (2×10 mL) and brine (10 mL). Drying (MgSO$_4$), concentration, and chromatography (silica gel, 2:1 hexane:ethyl acetate) gave the title compound (0.87 g, 87%) as a colorless oil: TLC R$_f$ 0.44 (silica gel, 2:1 hexane:ethyl acetate); $^1$H NMR (250 MHz, CDCl$_3$) mixture of amide rotamers; δ 7.75–8.00 (m, 2H), 7.15–7.45 (m, 5H), 7.00–7.15 (m, 1H), 5.72–5.92 (m, 1H), 4.91–5.25 (m, 3H), 4.45–4.63 (m, 2H), 3.66 (s, 3H), 3.13 and 2.89 (2× s, 3H), 2.58–2.94 (m, 2H), 1.56 (s,9H); IR (CCl$_4$) 3415, 3260, 1736, 1716, 1652, 1497, 1368, 1296, 1252, 1207, 1163, 1117, 1109 cm$^{-1}$; MS(ES) m/e 1027 [2M+Na]$^+$, 1005 [2M+H]$^+$, 503 [M+H]$^+$, 447 [M+H-C$_4$H$_8$]$^+$.

e) t-butyl (S)-4-fluoro-3-[[[4-methoxy-1,4-dioxo-2-aminobutyl]methylamino]methyl]benzoate A mixture of the compound of Example 28(d) (0.87 g, 1.73 mmol), 10% Pd/C (184 mg, 0.17 mmol), and methanol (17 mL) was shaken at RT under hydrogen (50 psi). After 1.5 h, the reaction was filtered through Celite® and concentrated. Chromatography (silica gel, 10% methanol in 1:1 ethyl acetate:chloroform) gave the title compound (579.8 mg, 91%) as a colorless oil: TLC R$_f$ 0.50 (silica gel, 10% methanol in 1:1 ethyl acetate:chloroform); $^1$H NMR (250 MHz, CDCl$_3$) mixture of amide rotamers; δ 7.80–8.05 (m, 2H), 7.02–7.18 (m, 1H), 4.55–4.88 (m, 2H), 4.15–4.28 (m, 1H), 3.71 and 3.70 (2× s, 3H), 3.11 and 2.95 (2× s, 3H), 2.76 (dd, J=16.3, 5.4 Hz, 1H), 2.48–2.67 (m, 1H), 1.74 and 1.57 (2× s, 9H); IR (CCl$_4$) 3380, 1735, 1717, 1653, 1370, 1298, 1253, 1164, 1112 cm$^{-1}$; MS(ES) m/e 369 [M+H]$^+$, 313 [M+H-C$_4$H$_8$]$^+$.

f) methyl (S)-(−)-2,3,4,5-tetrahydro-7-(t-butoxycarbonyl)-4-methyl-3-oxo-1H-1,4-benzodiazepine-2-acetate A solution of the compound of Example 28(f) (416.1 mg, 1.13 mmol) and 2,6-di-t-butylpyridine (0.51 mL, 2.26 mmol) in anhydrous dimethyl sulfoxide (5.7 mL) was heated under argon in an oil bath at 120–125° C. After 17.5 h, the reaction was cooled in ice-water and diluted with water. The mixture was extracted with ethyl acetate, and the combined ethyl acetate layers were washed with water and brine. Drying (MgSO$_4$), concentration, and chromatography (silica gel, 3:2 ethyl acetate:hexane) gave the title compound (221.8 mg, 56%) as a nearly colorless solid: TLC R$_f$ 0.41 (3:2 ethyl acetate/hexane); [α]$_D$ −202.7° (c 1.0,CH$_3$OH); $^1$H NMR (400 MHz, CDCl$_3$) δ 7.68 (dd, J=8.5, 1.8 Hz, 1H), 7.59 (d, J=1.8 Hz, 1H), 6.50 (d, J=8.5 Hz, 1H), 5.44 (d, J=16.4 Hz, 1H), 5.08–5.16 (m, 1H), 4.54 (br d, J=4.5 Hz, 1H), 3.76 (d, J=16.4 Hz, 1H), 3.75 (s, 3H), 3.08 (s,3H), 3.00 (dd, J=16.0, 6.9 Hz, 1H), 2.67 (dd, J=16.0, 6.3 Hz, 1H), 1.57 (s, 9H); IR (chloroform) 3560–3240 (br), 1731, 1695, 1663, 1610, 1369, 1302, 1252, 1171, 1146, 1134 cm$^{-1}$; MS(ES) m/e 719 [2M+Na]$^+$, 697 [2M+H]$^+$, 349 [M+H]$^+$.

g) methyl (S)-(−)-7-carboxy-2,3,4,5-tetrahydro-4-methyl-3-oxo-1H-1,4-benzodiazepine-2-acetate A solution of the compound of Example 28(f) (176.4 mg, 0.506 mmol) in anhydrous dichloromethane (2.5 mL) was cooled to 0° C. and deoxygenated through three evacuation/argon flush cycles. TFA (2.5 mL) was added dropwise over 3 min, and the resulting solution was stirred for 2 h, during which time the temperature rose to +15° C. The reaction was concentrated (20° C.) and the residue was reconcentrated from toluene (35° C.) to remove any residual TFA and give the title compound.

h) methyl (S)-(−)-7-[1-[1'-(t-butoxycarbonyl)-4,4'-bipiperidinyl]carbonyl]-2,3,4,5-tetrahydro-4-methyl-3-oxo-1H-1,4-benzodiazepine-2-acetate The compound of Example 28(g), 1-hydroxybenzotriazole hydrate (82 mg, 0.607 mmol), and 4-(t-butoxycarbonyl)-4,4'-bipiperidine (163 mg, 0.607 mmol) were dissolved in anhydrous dimethylformamide (2.5 mL), and the solution was cooled to 0° C. under argon. Diisopropylethylamine (0.18 mL, 1.01 mmol) was added, followed by 1-(3-dimethylaminopropyl)-3-ethylcarbodiimide hydrochloride (116 mg, 0.607 mmol), and the reaction was warmed to RT. After 21 h, the reaction was concentrated and the residue was partitioned between water and chloroform. The layers were separated and the aqueous layer was extracted with chloroform. Drying (MgSO$_4$), concentration, and chromatography (silica gel, 10% methanol in 1:1 ethyl acetate:chloroform) gave the title compound (215.4 mg, 78%) as a yellow foam: TLC R$_f$ 0.50 (10% methanol in 1:1 ethyl acetate:chloroform); [α]$_D$ −140.2° (c 1.0,CH$_3$OH); $^1$H NMR (400 MHz, CDCl$_3$) δ 7.08–7.15 (m, 2H), 6.52 (d, J=8.3 Hz, 1H), 5.44 (dd, J=16.4 Hz, 1H), 5.06 (t, J=6.6 Hz, 1H), 3.90–4.80 (br m, 4H), 3.75 (s, 3H), 3.73 (d, J=16.4 Hz, 1H), 3.08 (s, 3H), 2.99 (dd, J=15.8, 6.6 Hz, 1H), 2.56–2.93 (m, 5H), 1.60–1.83 (m, 4H), 1.46 (s, 9H), 1.08–1.42 (m, 6H); IR (CCl$_4$) 3290, 1735, 1689, 1669, 1610, 1436, 1426, 1365, 1286, 1173 cm$^{-1}$; MS(ES) m/e 1085 (2M+H)$^+$, 565 [M+Na]$^+$, 543 [M+H]$^+$, 502, 487 [M+H-C$_4$H$_8$]$^+$.

i) (S)-(−)-7-[1-[1'-(t-butoxycarbonyl)-4,4'-bipiperidinyl]-carbonyl]-2,3,4,5-tetrahydro-4-methyl-3-oxo-1H-1,4-benzodiazepine-2-acetic acid Using the procedure of Example 27(b)–(c), the compound of Example 28(h) was converted to the title compound.

Example 29

Preparation of (S)-7-[(4,4'-bipiperidin-1-yl) carbonyl]-2,3,4,5-tetrahydro-4-methyl-3-oxo-1H-1, 4-benzodiazepine-2-acetic acid a) 4-fluoro-3-cyanobenzoic acid To a mixture of 2-fluoro-5-methylbenzonitrile (13.5 g, 0.1 mol), tetrabutylammonium bromide (1.61 g, 5 mmol), and ruthenium(III)chloride trihydrate (0.261 g, 1 mmol) in dichloromethane (150 mL) was added a solution of sodium hypochlorite (645 mL, 0.45 mol) which had been neutralized to pH 9 with 20% sulfuric acid. The reaction mixture was stirred and maintained at pH 9 by adding 20% sodium hydroxide solution at RT. After 3 h, the aqueous phase was separated and neutralized to pH 2 with 20% sulfuric acid and the solid which formed was filtered to give the title compound (3.4 g, 20%). mp 177–8° C. $^1$H NMR (CDCl$_3$) δ 7.35 (t, J=8.70 Hz, 1H), 8.38 (m, 1H), 8.42 (m, 1H).

b) t-butyl 4-fluoro-3-cyanobenzoate

To a stirred solution of the compound of Example 29(a) (100 mg, 0.6 mmol) in toluene (20 mL) at 80° C. was added a solution of N,N-dimethylformamide di-t-butyl acetal (1 mL, 4 mmol) in toluene (2 mL) over 10 min. The reaction mixture was heated for 1 h, cooled, washed with saturated sodium bicarbonate, dried (MgSO$_4$), and concentrated to give the title compound (70 mg, 52%). MS(ES) m/e 222 [M+H]$^+$. $^1$H NMR (CDCl$_3$) δ 1.60 (9H, s), 7.29 (t, J=8.62 Hz, 1H) 8.25 (m, 1H), 8.28 (m, 1H).

c) N-[[2-cyano-4-t-butoxycarbonyl]phenyl]-L-aspartic acid β-methyl ester

A mixture of the compound of Example 29(b) (6 g, 27 mmol), L-aspartic acid β-methyl ester hydrochloride (6.1 g, 33 mmol), and sodium bicarbonate (8.37 g, 100 mmol) in water (20 mL) and dimethyl sulfoxide (80 mL) was heated at 72° C. for 24 h. The reaction mixture was diluted with ice cold dilute hydrochloric acid and extracted with ethyl acetate. The combined organic phase was extracted with cold saturated aqueous sodium bicarbonate. The basic extracts were combined, acidified to pH 2 with cold dilute hydrochloric acid, and extracted with ethyl acetate. The combined organic extract was dried (MgSO$_4$), and concentrated to give the title compound (7.1 g, 75%), MS(ES) m/e 349 [M+H]$^+$; $^1$H NMR (CDCl$_3$) δ 1.57 (s, 9H), 3.01 (m, 2H), 3.75 (s, 1H), 4.64 (m, 1H), 5.77 (d, J=8.49 Hz, 1H), 6.71 (d, J=8.93 Hz, 1H), 8.02 (dd, J=8.93, 1.85 Hz, 1H), 8.08 (d, J=1.89 Hz, 1H).

d) N-[[2-formyl-4-t-butoxycarbonyl]phenyl]-L-aspartic acid β-methyl ester

The compound of Example 29(c) (7.0 g, 20 mmol) was dissolved in acetic acid (65 mL) and placed in a hydrogenation bottle. After cooling, wet Raney® nickel (14 g), water (65 mL) and pyridine (65 mL) were added. The resulting mixture was purged of oxygen with argon for 0.5 h, and shaken in a hydrogen atmosphere (50 psi) at 60° C. for 5 h. The mixture was degassed, filtered and the filtrate was azeotroped with toluene at 50° C. under high vacuum. The residual oil was taken up in ethyl acetate (300 mL) and washed with cold dilute hydrochoric acid, dried (MgSO$_4$), and concentrated to give the title compound as light orange amorphous solid (5.9 g, 84%). MS(ES) m/e 352 [M+H]$^+$; 1H NMR (CDCl$_3$) δ 1.59 (s, 9H), 3.00 (m, 2H), 3.74 (s, 1H), 4.77 (m, 1H), 6.73 (d, J=8.88 Hz, 1H), 8.03 (d, J=8.85 Hz, 1H), 8.20 (d, J=2.12 Hz, 1H), 9.20 (d, J=8.31 Hz, 1H), 9.88 (s, 1H).

e) N-[[2-(N-methyl)aminomethyl-4-t-butoxycarbonyl]phenyl]-L-aspartic acid β-methyl ester A solution of the compound of Example 29(d) (5.9 g, 16.7 mmol) in ethyl acetate (100 mL) in a hydrogenation bottle was purged of oxygen with argon for 0.5 h. Platinum oxide (0.6 g), anhydrous MgSO$_4$ (5.9 g, 49 mmol), and a solution of methylamine (3.2M in methanol, 150 mL, 480 mmol) were added. The resulting mixture was shaken in a hydrogen atmosphere (50 psi) for 5 h and let stand for 18 h at RT. After addition of acetic acid (75 mL) with cooling, the mixture was again shaken in a hydrogen atmosphere (50 psi) for 2 h, and filtered. The filtrate was concentrated and azeotroped with toluene and the residue was desalted through an XAD-2 (350 g) column eluted with water (1.5 L) followed by a 50% acetonitrile:water. Two fractions (300 mL) were collected, concentrated and the residue was freeze-dried to give an off-white powder. The powder was dissolved in dichloromethane (200 mL), concentrated and the residue was azeotroped with toluene, and dried to give the title compound (5.2 g, 85%). MS(ES) m/e 367 [M+H]$^+$.

f) methyl (S)-7-(t-butoxycarbonyl)-2,3,4,5-tetrahydro-3-oxo-4-methyl-1H-1,4-benzodiazepine-2-acetate To a solution of the compound of Example 29(e) (5.2 g, 14.2 mmol) and triethylamine (2.0 mL, 14.4 mmol) in dichloromethane (250 mL) at RT under an argon atmosphere was added benzotriazol-1-yloxy-tris(dimethylamino)phosphonium hexafluorophosphate (6.5 g, 14.7 mmol). The reaction mixture was stirred overnight at RT, and washed with an ice-cold solution of dilute hydrochoric acid, water, 5% sodium bicarbonate, saturated brine, and then dried (MgSO$_4$). The solution was filtered, concentrated and the residue was chromatographed (silica gel, 40% ethyl acetate:hexane) to give the title compound (1.1 g, 22%). MS(ES) m/e 349.2 [M+H]$^+$; $^1$H NMR (CDCl$_3$) δ 1.57 (s, 9H), 2.67 (dd, J=15.93, 6.30 Hz, 2H), 3.00 (dd, J=15.93, 6.77 Hz, 2H), 3.08 (s, 3H), 3.75 (s, 1H), 3.76 (d, J=16.44 Hz, 1H) 4.51 (d, J=4.61, 1H), 5.11 (m, 1H) 5.45 (d, J=16.44 Hz, 1H), 6.50 (d, J=8.44 Hz, 1H), 7.55 (d, J=1.88 Hz, 1H), 8.20 (dd, J=8.48, 1.88 Hz, 1H); [α]$_D$ –225.1° (c 1,CH$_3$OH).

g) methyl (S)-7-carboxy-2,3,4,5-tetrahydro-3-oxo-4-methyl-1H-1,4-benzodiazepine-2-acetate To a solution of the compound of Example 29(f) (160 mg, 0.46 mmol) in dichloromethane (5 mL) was added 4M hydrogen chloride:dioxane (5 mL, 20 mmol) at RT under argon. The reaction mixture was stirred for 18 h. The suspension was concentrated to give the title compound as an off-white solid.

h) methyl (S)-7-[(4-t-butoxycarbonyl-4'-bipiperidin)-1-ylcarbonyl]-2,3,4,5-tetrahydro-4-methyl-3-oxo-1H-1,4-benzodiazepine-2-acetate The compound of Example 29(g), 1-hydroxybenzotriazole (75 mg, 0.55 mmol), and 4-t-butoxycarbonyl-4'-bipiperidine were dissolved in anhydrous dimethylformamide (2.5 mL). Diisopropylethylamine (0.16 mL, 0.92 mmol) was added, followed by 1-(dimethylaminopropyl)-3-ethylcarbodiimide hydrochloride (105 mg, 0.55 mmol), and the reaction mixture was stirred overnight at RT under argon. The reaction mixture was partitioned between ice water (50 mL) and ethyl acetate (30 mL). The layers were separated and the aqueous phase was extracted with ethyl acetate (2×30 mL). The combined organic extract was dried (MgSO$_4$), concentrated and the residue was chromatographed (silica gel, 2% methanol:dichloromethane) to give the title compound (162 mg, 59%). MS(ES) m/e 599.0 [M+H]$^+$; $^1$H NMR (CDCl$_3$) δ 1.45 (s, 9H), 1.20 (m, 6H), 1.70 (m, 4H), 2.66 (dd, J=16.08, 6.04 Hz, 2H), 2.81 (br s, 4H), 2.98 (dd, J=16.08, 7.31 Hz, 2H), 3.06 (s, 3H), 3.71 (d, J=16.44 Hz, 1H), 3.73 (s, 1H), 3.76 (d, J=16.44 Hz, 1H) 4.13 (br s, 4H), 5.07 (m, 1H) 5.45 (d, J=16.44 Hz, 1H), 6.52 (d, J=8.51 Hz, 1H), 7.09 (m, 2H); [α]$_D$ –139.3° (c 1,CH$_3$OH).

i) (S)-7-[1-[1'-(t-butoxycarbonyl)-4,4'-bipiperidinyl] carbonyl]-2,3,4,5-tetrahydro-4-methyl-3-oxo-1H-1,4-benzodiazepine-2-acetic acid Using the procedure of Example 27(b–c), the compound of Example 29(h) was converted to the title compound.

Example 30

Preparation of (S)-7-[[4,4'-bipiperidin-1-yl]carbonyl]-2,3,4,5-tetrahydro-4-methyl-3-oxo-1H-1,4-benzodiazepine-2-acetic acid a) (S)-7-[[1'-(t-butoxycarbonyl)-4,4'-bipiperidin-1-yl]carbonyl]-2,3,4,5-tetrahydro-4-methyl-3-oxo-1H-1,4-benzodiazepine-2-acetic acid The compound of Example 27(a) (2.85 g, 5.3 mmol) was taken up in 1:1 methanol:THF (30 mL), purged with argon, cooled and treated with 1N sodium hydroxide (6.3 mL, 6.3 mmol). The resulting solution was stirred at RT for 16 h under argon. The solution was concentrated, diluted with water (10 mL), and adjusted to pH 5 with 1M acetic acid (litmus paper). The solution was filtered and the solid was dried in vacuo to give title compound (2.46 g, 87%).

b) (S)-7-[[4,4'-bipiperidin]-1-ylcarbonyl]-2,3,4,5-tetrahydro-4-methyl-3-oxo-1H-1,4-benzodiazepine-2-acetic acid The compound of Example 30(a) (1.46 g, 2.77 mmol) was treated with 4M hydrogen chloride in dioxane (30 mL) for 1 h under argon. The solution was concentrated and the residue was taken up in water and adjusted to pH 9 (litmus paper) with concentrated ammonium hydroxide and the resulting solution was loaded onto an XAD-2 column (3×7.5 cm). The column was eluted with water followed by 50% acetonitrile:water. Fractions containing the product were combined and lyophilized to give the title compound (910 mg, 77%) which was recrystallized from aqueous acetone. mp (shrinking 193) 218–220° C.; $^1$H NMR (400 MHz, DMSO$_{d6}$) δ 1.0–3.9 (m, 26H), 6.5–8.5 (m, 5H); MS (ES) m/e 429.2 [M+H]$^+$; HPLC k' 5.37 (VyDac C18, 4.5×250 mm, gradient, A:acetonitrile B:water-0.1% TFA, 5%–60% acetonitrile in 20 min, UV detection at 220 nm); [α]$_D$ −180.3° (c 1, MeOH); Anal. (C$_{23}$H$_{32}$N$_4$O$_4$.2.33 H$_2$O) calcd: C, 58.71; H, 7.81; N, 11.91. found: C, 58.67; H, 7.79; N, 11.80.

Example 31

Preparation of (R,S)-7-[(4,4'-bipiperidin-1-yl) carbonyl]-2,3,4,5-tetrahydro-4-methyl-3-oxo-1H-1,4-benzodiazepine-2-acetic acid Using the procedure of Example 30, except substituting the compound of Example 8(j) for the compound of Example 27(a), gave the title compound as a crystalline solid. mp (shrinking 193° C.) 219–220° C.; MS(ES) m/e 429 [M+H]$^+$; HPLC k' 6.5 (Ultrasphere ODS, 4.5×250 mm, gradient, A:acetonitrile B:water-0.1% trifluroracetic acid, 5–60% acetonitrile durings 20 min, UV detection at 220 nm).

Example 32

Preparation of Sodium (R,S)-7-[(4,4'-bipiperidin-1-yl)carbonyl]-2,3,4,5-tetrahydro-4-methyl-3-oxo-1H-1,4-benzodiazepine-2-acetate The compound of Example 31 (10 mg, 0.023 mmol) was taken up in water (1 mL) and 1M sodium hydroxide (0.024 mL, 0.024 mmol) was added. The resulting solution was lyophilized and the powder was crystallized from aqueous acetone to give the title compound as a crystalline solid (2 mg). mp 220–223° C. [shrinking 204° C.].

Example 33–34 a) The compound of Example 1(a) was separated by chiral HPLC to give the following compounds: 33(a). methyl (R)-8-[[[2-[N-(benzyloxycarbonyl)-4-piperidinyl]ethyl] methylamino]carbonyl]-2,3,4,5-tetrahydro-4-methyl-3-oxo-1H-1,4-benzodiazepine-2-acetate: HPLC t$_R$ 30.4 min (Chiralpak AS, 4.6×250 mm, 8 mL/min, 1:1 hexane:ethanol-0.5% diethylamine, UV detection at 325 nm); HPLC t$_R$ 25.8 min (Ultrasphere C18, 4.6×250 mm, gradient, A: acetonitrile B: water-0.1% TFA, 5–60% acetonitrile over 20 min, UV detection at 220 nm) 34(a) methyl (S)-8-[[[2-[N-(benzyloxycarbonyl)-4-piperidinyl]ethyl]methylamino] carbonyl]-2,3,4,5-tetrahydro-4-methyl-3-oxo-1H-1,4-benzodiazepine-2-acetate: HPLC t$_R$ 22.1 min (Chiralpak AS, 21.2×250 mm, 8 mL/min, 1:1 hexane:ethanol-0.5% diethylamine, UV detection at 254 nm); HPLC t$_R$ 25.9 min (Ultrasphere C18, 4.6×250 mm, gradient, A: acetonitrile B: water-0.1% TFA, 5–60% acetonitrile over 20 min, UV detection at 325 nm).
b) The compounds of Examples 33(a) and 34(a) (100 mg) were separately dissolved in methanol (15 mL) containing acetic acid (20 drops) were treated with 10% Pd/C (50 mg) and shaken in a hydrogen atmosphere for 5 h. The mixture was filtered through Celite® and concentrated to give the following compounds: 33(b). methyl (R)-2,3,4,5-tetrahydro-4-methyl-3-oxo-8-[[[2-(4-piperidinyl)ethyl]methylamino] carbonyl]-1H-1,4-benzodiazepine-2-acetate. HPLC t$_R$ 15.6 min (Ultrasphere C 18, 4.6×250 mm, gradient, A: acetonitrile B: water-0.1% TFA, 5–60% acetonitrile over 20 min, UV detection at 220 nm) 34(b). methyl (S)-2,3,4,5-tetrahydro-4-methyl-3-oxo-8-[[[2-(4-piperidinyl)ethyl] methylamino]carbonyl]-1H-1,4-benzodiazepine-2-acetate. HPLC t$_R$ 15.5 min (Ultrasphere C18, 4.6×250 mm, gradient, A: acetonitrile B: water-0.1% TFA, 5–60% acetonitrile over 20 min, UV detection at 220 nm).
c) Using the procedure of Example 1(c), except sub-stituting the compound of Examples 33(b) and 34(b) for the compound of Example 1(b) yielded the following compounds: 33(c). (R)-2,3,4,5-tetrahydro-4-methyl-3-oxo-8-[[[2-(4-piperidinyl)ethyl]methylamino]carbonyl]-1H-1,4-benzodiazepine-2-acetic acid: $^1$H NMR (DMSO-d$_6$) δ 6.4–8.6 (m, 5H), 5.0–5.6 (m, 2H), 1.0–3.9 (m, 22H); [α]$_D$ +82.3 (c 0.3, CH$_3$OH); MS(ES) m/e 403 [M+H]$^+$, [M−H]$^−$ 401; HPLC k' 5.0 HPLC t$_R$ 15.6 min (Ultrasphere C18, 4.6×250 mm, gradient, A: acetonitrile B: water-0.1% TFA, 5–60% acetonitrile over 20 min, UV detection at 220 nm); Anal. (C$_{21}$H$_{30}$N$_4$O$_4$.2.25 C$_2$HF3O$_2$.2.75 H$_2$O) calcd: C, 50.44; H, 5.78; N, 9.94. found: C, 50.42; H, 5.89; N, 10.17 34(c). (S)-2,3,4,5-tetrahydro-4-methyl-3-oxo-8-[[[2-(4-piperidinyl)ethyl]methylamino]carbonyl]-1H-1,4-benzodiazepine-2-acetic acid: $^1$H NMR (DMSO-d$_6$) δ 6.4–8.6 (m, 5H), 5.0–5.6 (m, 2H), 1.0–3.9 (m, 22H); [α]$_D$ −110 (c 0.45, CH$_3$OH); MS(ES) m/e 403 [M+H]$^+$, [M−H]$^−$ 401; HPLC k' 5.0 HPLC t$_R$ 15.6 min (Ultrasphere C18, 4.6×250 mm, gradient, A: acetonitrile B: water-0.1% TFA, 5–60% acetonitrile over 20 min, UV detection at 220 nm); Anal. (C$_{21}$H$_{30}$N$_4$O$_4$.1.5 C$_2$HF$_3$O$_2$.1.25 H$_2$O) calcd: C, 43.22; H, 5.37; N, 7.91. found: C, 43.10; H, 5.17; N, 8.11.

Example 35

Preparation of (S)-2,3,4,5-tetrahydro-4-methyl-3-oxo-8-[[[2-(4-piperidinyl) ethyl]methylamino] carbonyl]-1H-1,4-benzodiazepine-2-acetic acid a) t-butyl (S)-4-[N-(t-butoxycarbonyl)-(methylamino)-methyl]-3-[2-(1,4-dimethoxy-1,4-dioxo-2-butyl)amino] benzoate A solution of t-butyl 3-amino-4-[N-(t-butoxycarbonyl)-N-(methyl)-aminomethyl]benzoate (10.4 g, 0.03 mol) in dichloromethane (75 mL) was treated with a solution of dimethyl (R)-2-(trifluoromethylsulfonyloxy)-succinate [*Liebigs Ann. Chem.*, 314–333 (1986)] (8.8 g, 0.03 mol) and 2,6-di-t-butylpyridine (6 g, 0.03 mol) in dichloromethane (10 mL) and the mixture was stirred for 4 d. The mixture was washed with dilute hydrochoric acid, and the organic phase was washed with aqueous sodium carbonate, dried (MgSO$_4$) and concentrated. The residue was chromatographed (silica gel, 10% ethyl acetate:hexane) and concentrated to give the title compound (73%).
b) t-butyl (S)-4-(methylamino)methyl-3-[2-(1,4-dimethoxy-1,4-dioxo-2-butyl)amino]benzoate A solution of the compound of Example 35(a) (13 g, 0.027 mol) in dichloromethane (25 mL) was treated with 4M hydrogen chloride in dioxane (60 mL), stirred for 45 min, and washed with 5% sodium carbonate. The organic phase was dried (MgSO$_4$) and concentrated to give the title compound (6.5 g).
c) methyl (S)-8-(t-butoxycarbonyl)-2,3,4,5-tetrahydro-4-methyl-3-oxo-1H-1,4-benzodiazepine-2-acetate A solution of the compound of Example 35(b) (6.5 g, 0.015 mol) in xylene (100 mL) was heated to 130° C. for 14.5 h, cooled, and concentrated. The residue was stirred with ether, filtered, and concentrated. The residue was chromatographed (silica gel, 0.5–0.75% methanol:dichloromethane) and fractions containing product were pooled, concentrated, diluted with ether and stored in the cold for 3 days. The mixture was filtered and the filtrate was concentrated to give the title compound (2.7 g, 52%).

d) methyl (S)-8-carboxy-2,3,4,5-tetrahydro-4-methyl-3-oxo-1H-1,4-benzodiazepine-2-acetate hydrochloride The compound of Example 35(c) (2.8 g) in dichloromethane (10 mL) was treated with 4M hydrogen chloride in dioxane (25 mL) and stirred for 16 h. The mixture was concentrated to give the title compound.

e) methyl (S)-2,3,4,5-tetrahydro-4-methyl-3-oxo-8-[[[2-[N-trifluoroacetyl-4-piperidinyl]ethyl]methylamino]carbonyl]-1H-1,4-benzodiazepine-2-acetate The compound of Example 35(d) (310 mg, 1.1 mmol) and diisopropylethylamine (285 mg, 2.2 mmol) in dimethylformamide (2.5 mL) was added to a mixture of N-methyl-2-(N-trifluoroacetyl-4-piperidinyl)ethylamine hydrochloride (300 mg, 1.1 mmol), diisopropylethylamine (140 mg, 1.1 mmol), and 1-hydroxybenzotriazole hydrate (150 mg, 1.1 mmol) in dimethylformamide (2.5 mL) followed by 1-(3-dimethylaminopropyl)-3-ethylcarbodiimide hydrochloride (220 mg, 1.1 mmol). The mixture was stirred for 16 h, concentrated and the residue was triturated with ethyl acetate and water. The combined organic phase was washed with brine, dried ($MgSO_4$) and concentrated. The residue was chromatographed (silica gel, 0.5–1.5% methanol:dichloromethane) and fractions containing the product were combined and concentrated to give the title compound (260 mg, 51%). $[\alpha]_D$ –75.6 (c 1,$CH_3OH$); MS(ES) m/e 513 $[M+H]^+$; 557 $[M+HCO_2^-]^-$; HPLC $t_R$ 8.22 min (WHELK-O, 4.6×25 mm, 1 mL min, 10% methanol:water, UV detection at 220 nM); Anal. ($C_{24}H_{31}F_3N_4O_5 \cdot 1.5 H_2O$) calcd: C, 53.33; H, 6.34; N, 10.36 found: C, 53.39, H, 6.23; N, 9.98.

f) (S)-2,3,4,5-tetrahydro-4-methyl-3-oxo-8-[[[2-[4-piperidinyl]ethyl]methylamino]carbonyl]-1H-1,4-benzodiazepine-2-acetic acid The compound of Example 35(e) was stirred with sodium hydroxide in methanol/water to give the title compound.

Example 36

Preparation of methyl (S)-7-t-butoxycarbonyl-2,3,4,5-tetrahydro-3-oxo-2-(2-phenylethyl)-1H-2-benzazepine-4-acetate a) methyl 5-(t-butoxycarbonyl)-2-[N-(butoxycarbonyl)-N-(2-phenylethyl)aminomethyl]cinnamate To a stirred solution of the compound of Preparation 8(d) (4.9 g, 10 mmol) in dry acetonitrile (15 mL) was added methyl acrylate (3 mL, 40 mmol), diisopropylethylamine (3.5 mL, 20 mmol), tri-o-tolylphoshine (304 mg, 1 mmol) and palladium acetate (112 mg, 0.5 mmol). The reaction was repeatedly evacuated and flushed with argon and then heated to 80° C. After 1 h, an additional amount of tri-o-tolylphoshine (304 mg, 1 mmol) and palladium acetate (112 mg, 0.5 mmol) was added and the reaction was stirred for 2 h. The reaction was then cooled to RT, concentrated, suspended with ether (100 mL) and petroleum ether (50 mL), filtered free of insoluble materials and concentrated. The residual oil was purified by flash chromatography (silica gel, 15% ethyl acetate:hexane) to give the title compound (4.91 g, 99%). $^1$H NMR ($CDCl_3$, 400 MHz) (mixture of amide rotomers) δ 1.42 and 1.49 (9H, 2 br s), 1.60 (9H, s), 2.74 and 2.84 (2H, 2 br s), 3.28 and 3.42 (2H, 2 br s), 3.82 (3H, s), 4.47 and 4.57 (2H, 2 br s), 6.43 (1H, d, J=14.8 Hz), 7.05–7.30 (6H, m), 7.82–7.92 (1H, m), 7.97 (1H, dd), 8.15 (1H, d, J=1.4 Hz).

b) methyl 5-(t-butoxycarbonyl)-2-[N-(butoxycarbonyl)-N-(2-phenylethyl)aminomethyl]phenylpropionate The compound of Example 36(a) (4.91 g, 9.9 mmol) was hydrogenated at 55 psi $H_2$ over 10% Pd/C (2.5 g) in methanol (100 mL) for 7 h. After filtration through a pad of Celite® and concentration, the remaining oil was purified by flash chromatography (silica gel, 15% ethyl acetate:hexane) to give title compound as a clear oil (4.48 g, 91%). $^1$H NMR ($CDCl_3$, 400 MHz) (mixture of amide rotomers) δ 1.42 and 1.49 (9H, 2 br s), 1.60 (9H, s), 2.58 (2H, t), 2.77 and 2.82 (2H, 2 br s), 2.92 (2H, br s), 3.31 and 3.42 (2H, 2 br s), 3.70 (3H, s), 4.38 and 4.47 (2H, 2 br s), 7.07–7.31 (6H, m), 7.78 (1H, s), 7.81 (1H, dd).

c) 5-(t-butoxycarbonyl)-2-[N-(butoxycarbonyl)-N-(2-phenylethyl)aminomethyl]phenylpropionic acid The compound of Example 36(b) (4.48 g, 9 mmol) was treated with 1N sodium hydroxide (10 mL) in dioxane (50 mL) for 16 h at RT. After acidification with 1N hydrochloric acid (10 mL), the reaction was extracted with ethyl acetate (2×100 mL), washed with brine, dried ($MgSO_4$), filtered and concentrated to give the title compound as a white solid (4.12 g, 95%). TLC $R_f$ 0.5 (silica gel, 95:4:1, chloroform:methanol:acetic acid).

d) 5-(t-butoxycarbonyl)-2-[N-(butoxycarbonyl)-N-(2-phenylethyl)aminomethyl]phenylpropionyl fluoride To a stirred solution of the compound of Example 36(c) (4.12 g, 8.5 mmol) under argon in dry dichloromethane (25 mL) was added pyridine (0.73 mL, 9 mmol) followed by cyanuric fluoride (0.56 mL, 6.1 mmol). After stirring for 2 h, the reaction became a thick suspension. The reaction was then concentrated, taken up in ether (100 mL) and, filtered through a pad of Celite to remove insoluble materials. The filtrate was washed with cold water, dried ($MgSO_4$), filtered and concentrated to give the title compound as a clear oil (4.21 g, 96%).

e) 4(R)-benzyl-3-[3-[5-(t-butoxycarbonyl)-2-[N-(t-butoxycarbonyl)-N-(2-phenylethyl)aminomethyl]phenyl]propionyl]-2-oxazolidinone To a stirred solution of (R)-4-benzyl-2-oxazolidinone (1.8 g, 10 mmol) in dry THF (25 mL) at –78° C. under argon was added via syringe, dropwise, a solution of 2.5N n-butyllithium in hexane (3.8 mL). After stirring for 15 min, a solution of the above the compound of Example 36(d) (4.21 g, 8.5 mmol) in THF (10 mL) was added dropwise over 5 min. The reaction was stirred for 1 h at –78° C. and quenched with saturated aqueous ammonium chloride (50 mL). The reaction was allowed to warm to RT, extracted with ethyl acetate, dried ($MgSO_4$), filtered and concentrated. The residue was purified by flash chromatography (silica gel, 25% ethyl acetate:hexane) to give the title compound as a white solid (5.13 g, 89%). $^1$H NMR ($CDCl_3$, 400 MHz) (mixture of amide rotomers) δ 1.42 and 1.49 (9H, 2 br s), 1.59 (9H, s), 2.75 (1H, dd), 2.78 (1H, m), 2.87 (1H, m), 3.01 (2H, m), 3.18 (1H, m), 3.23 (1H, dd), 3.31 (1H, dd), 3.33 (1H, m), 3.44 (1H, m), 4.18 (2H, m), 4.46 and 4.55 (2H, 2 br s), 4.67 (1H, m), 7.16 (6H, m), 7.29 (5H, m), 7.81 (1H, d), 7.82 (1H, s).

f) 4(R)-benzyl-3-[3-[5-(t-butoxycarbonyl)-2-[N-(t-butoxycarbonyl)-N-(2-phenylethyl)aminomethyl]phenyl]-2(S)-(methoxycarbonylmethyl)propionyl]-2-oxazolidinone To a stirred solution of the compound of Example 36(e) (5.13 g, 8 mmol) in dry THF (75 mL) with stirring at –78° C. under argon was added dropwise via syringe a solution of 1N lithium hexamethyldisilazane in THF (8.2 mL). After stirring for 15 min, methyl bromoacetate (3.75 mL, 40 mmol) was added in one portion. The reaction was allowed to warm to −28° C. and stirred for an additional 2 h, quenched with saturated aqueous ammonium chloride, extracted with ethyl acetate, washed with brine, dried (MgSO$_4$), filtered and concentrated. The residue was purified by column chromatography (silica gel, 20% ethyl acetate:hexane) to give the title compound as a white solid (3.00 g, 53%). HPLC k' 2.9, minor diastereomer k' 6.4, d.e.88% (Ultrasphere, 4.6×250 mm, 1.5 mL/min, 20% ethyl acetate:hexane, UV detection at 254 nm); $^1$H NMR (CDCl$_3$, 400 MHz) δ 1.40 and 1.47 (9H, 2 br s), 1.52 (9H, s), 2.44 and 2.52 (1H, br s and brd), 2.70 (1H, dd), 2.80 (2H, m), 2.88 (2H, m), 3.00 (1H, dd), 3.31 (1H, dd), 3.39 (2H, m), 3.67 (3H, s), 3.79 (1H, t), 4.00 (1H, d), 4.30 and 4.38 (1H, br s and br d), 4.55 (3H, m), 7.10–7.35 (11H, m), 7.72 (1H, s), 7.79 (1H, dd).

g) (S)-3-[5-(t-butoxycarbonyl)-2-[N-(t-butoxycarbonyl)-N-(2-phenylethyl)aminomethyl]phenyl]-2-(methoxycarbonylmethyl)-propionic acid hydrochloride To a stirred solution of the compound of Example 36(f) (1.47 g, 2 mmol) in (3:1) THF:water (16 mL) at 0° C. was added dropwise a solution of lithium hydroperoxide made from 30% hydrogen peroxide (0.7 mL) and lithium hydroxide hydrate (90 mg, 2.1 mmol) in water (2.1 mL). After stirring for 1 h at 0° C., excess peroxide was destroyed with a solution of sodium sulfite (1.28 g) in water (6.2 mL) dropwise with cooling. The reaction was then acidified with 3N hydrochloric acid and extracted with dichloromethane (2×50 mL), dried (MgSO$_4$), filtered and concentrated.

h) (S)-3-[5-(t-butoxycarbonyl)-2-[N-(t-butoxycarbonyl)-N-(2-phenylethyl)aminomethyl]phenyl]-2-(methoxycarbonylmethyl)-propionic acid hydrochloride The compound of Example 36(g) was treated with a solution of 4N hydrogen chloride in dioxane (15 mL) with stirring for 10 min at RT and concentrated without heating. The residue was taken up in ethyl acetate and concentrated to remove excess hydrogen chloride and crystallized from ethyl acetate:ether to give the title compound (0.75 g, 76%) as a white solid. $^1$H NMR (d$_4$-MeOH, 400 MHz) δ 1.60 (9H, s), 2.68 (1H, dd), 2.81 (1H, dd), 2.98–3.18 (5H, m), 3.42 (2H, m), 3.68 (3H, s), 4.40 (1H, d, J=13.6 Hz), 4.51 (1H, d, J=13.6 Hz), 7.32 (5H, m), 7.58 (1H, d, J=8.0 Hz), 7.90 (1H, dd), 7.95 (1H, d, J=1.4 Hz).

i) methyl (S)-7-(t-butoxycarbonyl)-2,3,4,5-tetrahydro-3-oxo-2-(2-phenylethyl)-1H-2-benzazepine-4-acetate To a stirred solution of the compound of Example 36(h) (0.35 g, 0.71 mmol) in dry N,N-dimethylformamide (20 mL) at 0° C. in a Dewer flask was added triethylamine (200 mL, 1.42 mmol), sodium bicarbonate (300 mg, 3.57 mmol), and diphenylphosphoryl azide (250 mL, 1.2 mmol). After stirring at 0° C. for 24 h, the reaction was concentrated, taken up in ethyl acetate (100 mL), washed with water, brine, dried (MgSO$_4$), filtered and concentrated. The residue was purified by chromatography (silica gel, 35% ethyl acetate:hexane) to give the title compound as a sticky white foam (243 mg, 78%). HPLC k' 2.13, k' 1.28 (enantiomer) >99.5% optically pure (Chiralpak AS, 0.46×250 mm, 1 mL/min, 20% EtOH:n-hexane, UV detection at 254 nm); [α]$_D$ −71.2 (c 1.4, MeOH); $^1$H NMR (CDCl$_3$, 400 MHz) δ 1.60 (9H, s), 2.42 (1H, dd), 2.74 (2H, t), 2.89 (1H, dd), 3.02 (2H, m), 3.60 (1H, m), 3.72 (3H, s), 3.81 (1H, d, J=16.7 Hz), 3.81 (1H, m), 5.20 (1H d, J=16.7 Hz), 7.00–7.23 (6H, m), 7.69 (1H, s), 7.71 (1H, d).

Example 37

Preparation of (R,S)-8-[[(4,4'-bipiperidin-1-yl]carbonyl]-2,3,4,5-tetrahydro-2-methyl-3-oxo-1H-2-benzazepine-4-acetic acid a) methyl (R,S)-8-carboxy-2,3,4,5-tetrahydro-2-methyl-3-oxo-1H-2-benzazepine-4-acetate Using the procedure of Preparation 8(a)–(g), except substituting 4-bromo-3-methylbenzoic acid for 3-bromo-4-methylbenzoic acid and substituting methylamine for phenethylamine, gave the title compound.

b) (R,S)-8-[[(4,4'-bipiperidin-1-yl)]carbonyl]-2,3,4,5-tetrahydro-2-methyl-3-oxo-1H-2-benzazepine-4-acetic acid Using the procedures of Example 25(b)–(c), except substituting the compound of Example 37(a) for the compound of Example 25(a), gave the title compound. HPLC k' 3.23 (PRP-1; 15% acetonitrile/water-0.1% TFA); $^1$H NMR (400 MHz, CD$_3$OD) δ 7.21–7.30 (m, 3H), 5.37 (d, J=16.6 Hz, 1H), 4.58–4.74 (m, 1H), 4.07 (d, J=16.6 Hz, 1H), 3.84–3.96 (m, 1H), 3.68–3.84 (m, 1H), 3.40 (br d, J=12.6 Hz, 2H), 3.17 (dd, J=17.7, 4.0 Hz, 1H), 2.69–3.17 (m, 6H), 3.01 (s, 3H), 2.47 (dd, J=17.0, 4.7 Hz, 1H), 1.10–2.10 (m, 10H); MS(ES) m/e 428.2 [M+H]$^+$, 214.6, 205.4; Anal. (C$_{24}$H$_{33}$N$_3$O$_4$.2 CF$_3$CO$_2$H.H$_2$O) calcd: C, 49.93; H, 5.54; N, 6.24. found: C, 50.17; H, 5.32; N, 6.20.

Example 38

Preparation of (R,S)-2,3,4,5-tetrahydro-7-[1-[4-(4-pyridyl)piperazinyl]carbonyl]-4-methyl-3-oxo-1H-1,4-benzodiazepine-2-acetic acid Methyl (R,S)-7-carboxy-2,3,4,5-tetrahydro-4-methyl-3-oxo-1H-1,4-benzodiazepine-2-acetate (2.0 mmol) dissolved in DMF (30 mL) was treated with 1-(3-dimethylaminopropyl)-3-ethylcarbodiimide hydrochloride (2.2 mmol), 1-HOBT (285 mg, 2.1 mmol) and adjusted to pH 7 with triethylamine. The mixture was treated with 1-(pyrid-4-yl)piperazine (2.4 mmol), stirred at RT for 48 h, concentrated and the residue was purified by flash chromatography to yield the title compound. HPLC k' 4.01 (PRP-1; 12% acetonitrile/water-0.1% TFA); $^1$H NMR (400 MHz, CD$_3$OD) δ 8.17 (d, J=7.4 Hz, 2H), 7.12–7.24 (m, 4H), 6.63 (d, J=9.0 Hz, 1H), 5.59 (d, J=16.7 Hz, 1H), 5.21 (dd, J=9.0, 5.1 Hz, 1H), 3.90 (d, J=16.7 Hz, 1H), 3.72–3.90 (m, 8H), 3.04 (s, 3H), 2.94 (dd, J=16.6, 9.0 Hz, 1H), 2.66 (dd, J=16.8, 5.1 Hz, 1H); MS(ES) m/e 424.2 [M+H]$^+$; Anal. (C$_{22}$H$_{25}$N$_5$O$_4$.2 CF$_3$CO$_2$H) calcd: C, 47.93; H, 4.18; N, 10.75. found: C, 47.86; H, 4.40; N, 10.87.

Example 39

Preparation of (R,S)-7-[[[4-(aminoiminomethyl)phenyl]-methylamino]carbonyl]-2,3,4,5-tetrahydro-2-[2-(2-thienyl)ethyl]-3-oxo-1H-2-benzazepine-4-acetic acid Using the procedure of Preparation 8(c)–(j), except substituting 2-(2-thienyl)ethanamine for 2-phenethylamine in the procedure of Preparation 8(c) and substituting sodium borohydride and nickel chloride hexahydrate for Pd/C and hydrogen in the procedure of Preparation 8(f) and substituting triethylamine in refluxing toluene for sodium methoxide in methanol in the procedure of Preparation 8(g) and substituting lithium hydroxide in aqueous THF for aqueous sodium hydroxide in methanol in the procedure of Preparation 8(j), gave the title compound.

Example 40

Preparation of (R,S)-2,3,4,5-tetrahydro-3-oxo-4-(2-phenylethyll)-7-[[[3-(4-piperidnyl]propyl]methylamino]-carbonyl]-1H-1,4-benzodiazepine-2-acetic acid Methyl (R,S)-7-carboxy-4-(2-phenylethyl)-1,3,4,5-tetrahydro-3-oxo-2H-1,4-benzodiazepine-2-acetate (2.0 mmol) dissolved in DMF (30 mL) was treated with benzotriazol-1-yloxy-tris(dimethylamino)phosphonium hexafluorophosphate (2.2 mmol), 1-HOBT (285 mg, 2.1 mmol) and adjusted to pH 7 with triethylamine. The mixture was treated with N-methyl-3-[N-(tert-butoxycarbonyl) piperidin-4-yl]]propanamine (2.4 mmol), stirred at RT for 48 h, concentrated and the residue was purified by flash chromatography.

The product is dissolved in 50% TFA/methlene chloride at RT and stirred 1 h. The solution is concentrated by evaporation of the TFA and methylene chloride, redissolved in methylene chloride and re-concentrated.

A portion of the compound (0.26 mmol) was dissolved in methanol (9 mL), and 1.0 N sodium hydroxide (0.81 mL, 0.81 mmol) was added. The solution was stirred at RT overnight, and concentrated. The residue was dissolved in water/acetonitrile (3 mL), cooled to 0° C., and acidified with TFA (0.21 mL, 2.7 mmol). The solution was concentrated and the residue was purified by reversed-phase flash chromatography (C-18 silica gel, AN/W-TFA). Concentration and lyophilization gave the title compound. MS(ES) m/e 507 [M+H]$^+$, 505 [M-H]$^-$.

Example 41

Preparation of (R,S)-2,3,4,5-tetrahydro-4-methyl-3-oxo-7-[[[3-(4-piperidnyl]propyl]methylamino] carbonyl]-1H-1,4-benzodiazepine-2-acetic acid Using the procedure of Example 40, except substituting the compound of Example 8(i) for methyl (R,S)-7-carboxy-4-(2-phenylethyl)-1,3,4,5-tetrahydro-3-oxo-2H-1,4-benzodiazepine-2-acetate, gave the title compound.

Example 42

Preparation of (R,S)-2,3,4,5-tetrahydro-4-isopropyl-3-oxo-8-[[[2-(4-piperidinyl) ethyl]methylamino] carbonyl]-1H-1,4-benzodiazepine-2-acetic acid a) methyl (R,S)-8-carboxy-2,3,4,5-tetrahydro-4-isopropyl-3-oxo-1H-1,4-benzodiazepine-2-acetate Using the procedure of Example 2(a) except substituting isopropylamine for isopentylamine and substituting diisopropylethylamine in refluxing xylene for sodium methoxide in methanol in the cyclization step gave the title compound.

b) methyl (R,S)-2,3,4,5-tetrahydro-4-isopropyl-3-oxo-8-[[[2-(4-pyridyl)ethyl]methylamino]carbonyl]-1H-1,4-benzodiazepine-2-acetate Using the procedure of Example 2(b), except substituting the compound of Example 42(a) for the compound of Example 2(b), gave the title compound.

c) methyl (R,S)-2,3,4,5-tetrahydro-4-isopropyl-3-oxo-8-[[[2-(4-piperidinyl) ethyl]methylamino]carbonyl]-1H-1,4-benzodiazepine-2-acetate Using the procedure of Example 2(c), except substituting the compound of Example 42(b) for the compound of Example 2(b), gave the title compound.

d) (R,S)-2,3,4,5-tetrahydro-4-isopropyl-3-oxo-8-[[[2-(4-piperidinyl)ethyl]methylamino]carbonyl]-1H-1,4-benzodiazepine-2-acetic acid Using the procedure of Example 2(d), except substituting the compound of Example 42(c) for the compound of Example 2(c), gave the title compound.

Example 43

Preparation of (S)-2,3,4,5-tetrahydro-4-(2-phenylethyl)-3-oxo-8-[[[2-(4-piperidinyl)ethyl] methylamino]carbonyl]-1H-1,4-benzodiazepine-2-acetic acid Using the procedure of Example 35, except substituting t-butyl 3-amino-4-[N-(t-butoxycarbonyl)-N-(2-phenylethyl) aminomethyl]benzoate for t-butyl 3-amino-4-[N-(t-butoxycarbonyl)-N-(methyl)-aminomethyl]benzoate in Example 35(a) gave the title compound.

Example 44

Preparation of (R,S)-7-[[[4-(aminoiminomethyl) phenyl]-carbonyl]methylamino]-2,3,4,5-tetrahydro-3-oxo-2-(2-phenylethyl]-1H-2-benzazepine-4-acetic acid a) methyl (R,S)-7-(benzyloxycarbonyl)amino-2,3,4,5-tetrahydro-3-oxo-2-(2-phenylethyl]-1H-2-benzazepine-4-acetate A mixture of methyl (R,S)-7-carboxy-2,3,4,5-tetrahydro-3-oxo-2-(2-phenylethyl)-1H-2-benzazepine-4-acetate (2.67 mmol), triethylamine (0.42 mL, 5.87 mmol) and diphenyl phosphorylazide (0.62 mL, 2.80 mmol) in toluene (20 mL) was heated at 105° C. for 0.5 h. After the temperature was lowered to 80° C., the mixture was treated with benzyl alcohol (0.60 mL, 0.42 mmol), stirred for 14 h and concentrated. The residue was purified by flash chromatography to give the title compound.

b) methyl (R,S)-7-[N-(benzyloxycarbonyl)methylamino]-2,3,4,5-tetrahydro-3-oxo-2-(2-phenylethyl]-1H-2-benzazepine-4-acetate The compound of Example 169(a) was treated with sodium hydride and iodomethane in 4:1 THF:dimethylformamide to give the title compound.

c) methyl (R,S)-7-methylamino-2,3,4,5-tetrahydro-3-oxo-2-(2-phenylethyl]-1H-2-benzazepine-4-acetate Using the procedure of Example 19(c), except substituting the compound of Example 169(b) for the compound of Example 19(b) gave the title compound.

d) methyl (R,S)-7-[[[4-(N-benzyloxycarbonyl) (aminoiminomethyl)phenyl]carbonyl]methylamino]-2,3,4,5-tetrahydro-3-oxo-2-(2-phenylethyl]-1H-2-benzazepine-4-acetate The compound of Example 169(b) is treated with 4-[N-(benzyloxycarbonyl)(aminoininomethyl)]benzoic acid, BOP and triethylamine in 5:4 dichloromethane:THF to give the title compound.

e) methyl (R,S)-7-[[[4-(aminoimiomethyl)phenyl] carbonyl]-amino]-2,3,4,5-tetrahydra-3-oxo-2-(2-phenylethyl]-1H-2-benzazepine-4-acetate Using the procedure of Example 19(c)–(d), except substituting the compound of Example 169(c) for the compound of Example 19(b) gave the title compound.

Example 45

Preparation of (R,S)-2,3,4,5-tetrahydro-3-oxo-4-methyl-8-[[[2-[(2-amino)pyrid-4-yl]ethyl] methylamino]carbonyl]-1H-1,4-benzodiazepine-2-acetic acid Methyl (R,S)-8-carboxy-4-methyl-1,3,4,5-tetrahydro-3-oxo-2H-1,4-benzodiazepine-2-acetate (2.0 mmol) dissolved in DMF (30 mL) was treated with benzotriazol-1-yloxy-tris (dimethylamino)phosphonium hexafluorophosphate (2.2 mmol), 1-HOBT (285 mg, 2.1 mmol) and adjusted to pH 7 with triethylamine. The mixture was treated with 2-[2-(amino)pyrid-4-yl]-N-(methyl)-ethanamine (2.4 mmol), stirred at RT for 48 h, concentrated and the residue was purified by flash chromatography.

A portion of the compound (0.25 mmol) was dissolved in methanol (9 mL), and 1.0 N sodium hydroxide (0.81 mL, 0.81 mmol) was added. The solution was stirred at RT overnight, and concentrated. The residue was dissolved in water/acetonitrile (3 mL), cooled to 0° C., and acidified with TFA (0.21 mL, 2.7 mmol). The solution was concentrated and the residue was purified by reversed-phase flash chromatography (C-18 silica gel, AN/W-TFA).

Example 46
Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 46
Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 47
Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:

1. A compound which is:
   (R,S)-7-[(4,4'-bipiperidin-1-yl)carbonyl]-2,3,4,5-tetrahydro-4-methyl-3-oxo-1H-1,4-benzodiazepine-2-acetic acid; or
   (S)-7-[(4,4'-bipiperidin-1-yl)carbonyl]-2,3,4,5-tetrahydro-4-methyl-3-oxo-1H-1,4-benzodiazepine-2-acetic acid, or a pharmaceutically acceptable salt thereof.

2. A pharmaceutical composition comprising a compound according to claim 1 and a pharmaceutically acceptable carrier.

3. A method for inhibiting platelet aggregation which comprises administering a compound according to claim 1 to a mammal in need thereof.

4. A method for treating myocardial infarction, thrombosis, embolism, stroke and infarct-related disorders, or restenosis following angioplasty, which comprises administering a compound according to claim 1 to a mammal in need thereof.

5. A method for inhibiting reocclusion of an artery or vein following thrombolytic therapy comprising administering a compound according to claim 1 and a thrombolytic agent.

6. A compound according to claim 1 which is (S)-7-[(4,4'-bipiperidin-1-yl)carbonyl]-2,3,4,5-tetrahydro-4-methyl-3-oxo-1H-1,4-benzodiazepine-2-acetic acid, or a pharmaceutically acceptable salt thereof.

7. A pharmaceutical composition comprising a compound according to claim 6 and a pharmaceutically acceptable carrier.

8. A method for treating acute myocardial infarction, deep vein thrombosis, pulmonary embolism, transient ischemia attack, unstable angina, stroke, infarct-related disorders, or restenosis following angioplasty, which comprises administering a compound according to claim 6 to a mammal in need thereof.

9. A pharmaceutical composition according to claim 2 comprising a 50 mg tablet.

10. A pharmaceutical composition according to claim 7 comprising a 50 mg tablet.

11. A method for inhibiting platelet aggregation which comprises administering a compound according to claim 6 to a mammal in need thereof.

12. A method for inhibiting reocclusion of an artery or vein following thrombolytic therapy comprising administering a compound according to claim 6 and a thrombolytic agent.

13. A method for inhibiting platelet aggregation which comprises administering a compound according to claim 6, and a cyclooxygenase inhibitor, thromboxane antagonist, thromboxane synthesis inhibitor, heparin, thrombin inhibitor, ADP receptor inhibitor or ticlopidine.

14. A method for inhibiting platelet aggregation which comprises administering a compound according to claim 6 and aspirin.

15. A method for inhibiting platelet aggregation which comprises administering a compound according to claim 6 and clopidogrel.

16. A process for preparing (S)-7-[(4,4'-bipiperidin-1-yl)carbonyl]-2,3,4,5-tetrahydro-4-methyl-3-oxo-1H-1,4-benzodiazepine-2-acetic acid, or a pharmaceutically acceptable salt thereof, which comprises treating a compound of the formula:

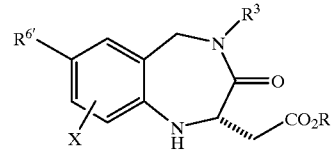

wherein
R is H, $C_{1-6}$alkyl, benzyl or a carboxy protecting group;
$R^3$ is methyl;
X is H; and
$R^{6'}$ is (4,4'-bipiperidin-1-yl)carbonyl wherein the basic nitrogen is protected;
with a reagent, in any order,
(i) to remove an amino protecting group from $R^{6'}$; and, if necessary,
(ii) to remove a carboxy protecting group from $CO_2R$; and
(iii) form a pharmaceutically acceptable salt thereof.

* * * * *